(12) United States Patent
Narciso, Jr.

(10) Patent No.: US 7,623,924 B2
(45) Date of Patent: Nov. 24, 2009

(54) DEVICES AND METHODS FOR GYNECOLOGIC HORMONE MODULATION IN MAMMALS

(75) Inventor: Hugh Louis Narciso, Jr., Santa Barbara, CA (US)

(73) Assignee: Leptos Biomedical, Inc., Fridley, MN (US)

( * ) Notice: Subject to any disclaimer, the term of this patent is extended or adjusted under 35 U.S.C. 154(b) by 524 days.

(21) Appl. No.: 11/215,892

(22) Filed: Aug. 30, 2005

(65) Prior Publication Data

US 2006/0079943 A1 Apr. 13, 2006

Related U.S. Application Data

(60) Provisional application No. 60/605,779, filed on Aug. 31, 2004.

(51) Int. Cl.
*A61N 1/02* (2006.01)
(52) U.S. Cl. ...................................................... 607/39
(58) Field of Classification Search .................. 607/39, 607/1–3, 45, 46
See application file for complete search history.

(56) References Cited

U.S. PATENT DOCUMENTS

| | | | |
|---|---|---|---|
| 3,733,407 A * | 5/1973 | Segre ......................... | 517/178 |
| 3,911,930 A | 10/1975 | Hagfors et al. | |
| 4,425,339 A * | 1/1984 | Pitchford .................... | 514/170 |
| 4,573,481 A | 3/1986 | Bullara | |
| 4,595,010 A | 6/1986 | Radke | |
| 4,629,449 A * | 12/1986 | Wong ......................... | 604/515 |
| 4,827,935 A | 5/1989 | Geddes et al. | |
| 4,867,164 A | 9/1989 | Zabara | |
| 5,095,905 A | 3/1992 | Klepinski | |
| 5,107,833 A | 4/1992 | Barsness | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |

(Continued)

FOREIGN PATENT DOCUMENTS

WO 98/57701 A1 12/1998

(Continued)

OTHER PUBLICATIONS

Bolte, et al., *Steroid Production from Plasma Cholesterol, II. In Vivo Conversion of Plasma Cholesterol to Ovarian Progesterone and Adrenal C10 and C21 Steroids in Humans*, JCE & M, 1974, vol. 38, No. 3, pp. 394-400.

(Continued)

*Primary Examiner*—Carl H Layno
*Assistant Examiner*—Jessica Reidel

(57) ABSTRACT

Methods and devices for electrically stimulating nerves and organs to induce and modulate the production of hormones according to desired hormone production patterns and hormone level patterns to treat gynecological conditions. Such methods and devices may be used to treat or alleviate the symptoms of menopause. In addition, such methods and devices may be used for birth control.

40 Claims, 8 Drawing Sheets

U.S. PATENT DOCUMENTS

| | | | |
|---|---|---|---|
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,515 A | 7/1994 | Rutecki et al. | |
| 5,335,657 A | 8/1994 | Terry, Jr. et al. | |
| 5,351,394 A | 10/1994 | Weinberg | |
| 5,423,872 A | 6/1995 | Cigaina | |
| 5,454,840 A | 10/1995 | Krakovsky et al. | |
| 5,458,626 A | 10/1995 | Krause | |
| 5,531,778 A | 7/1996 | Maschino et al. | |
| 5,540,730 A | 7/1996 | Terry, Jr. | |
| 5,540,734 A | 7/1996 | Zabara | |
| 5,571,150 A | 11/1996 | Wernicke et al. | |
| 5,690,691 A | 11/1997 | Chen et al. | |
| 5,707,400 A | 1/1998 | Terry, Jr. et al. | |
| 5,716,392 A | 2/1998 | Bourgeois et al. | |
| 5,725,563 A | 3/1998 | Klotz | |
| 5,755,750 A | 5/1998 | Petruska et al. | |
| 5,782,798 A | 7/1998 | Rise | |
| 5,836,994 A | 11/1998 | Bourgeois | |
| 5,919,216 A | 7/1999 | Houben et al. | |
| 5,928,272 A | 7/1999 | Adkins et al. | |
| 5,995,872 A | 11/1999 | Bourgeois | |
| 6,041,258 A | 3/2000 | Cigaina | |
| 6,068,596 A | 5/2000 | Weth et al. | |
| 6,109,269 A | 8/2000 | Rise et al. | |
| 6,129,685 A | 10/2000 | Howard, III | |
| 6,146,391 A | 11/2000 | Cigaina | |
| 6,165,180 A | 12/2000 | Cigaina | |
| 6,169,924 B1 | 1/2001 | Meloy et al. | |
| 6,174,665 B1 * | 1/2001 | Dullien | 435/4 |
| 6,308,105 B1 | 10/2001 | Duysens et al. | |
| 6,321,124 B1 | 11/2001 | Cigaina | |
| 6,350,455 B1 | 2/2002 | Donovan | |
| 6,356,786 B1 | 3/2002 | Rezai et al. | |
| 6,356,787 B1 | 3/2002 | Rezai et al. | |
| 6,381,495 B1 | 4/2002 | Jenkins | |
| 6,438,423 B1 | 8/2002 | Rezai et al. | |
| 6,497,718 B1 | 12/2002 | Dewan | |
| 6,558,320 B1 | 5/2003 | Causey et al. | |
| 6,587,719 B1 | 7/2003 | Barrett et al. | |
| 6,721,603 B2 | 4/2004 | Zabara et al. | |
| 6,885,888 B2 | 4/2005 | Rezai | |
| 2001/0014815 A1 | 8/2001 | Matsumura et al. | |
| 2002/0072780 A1 | 6/2002 | Foley | |
| 2002/0077675 A1 | 6/2002 | Greenstein | |
| 2002/0188336 A1 * | 12/2002 | Loncar et al. | 607/96 |
| 2003/0018367 A1 | 1/2003 | DiLorenzo | |
| 2003/0045909 A1 | 3/2003 | Gross et al. | |
| 2003/0144708 A1 | 7/2003 | Starkebaum | |
| 2003/0181958 A1 | 9/2003 | Dobak, III | |
| 2004/0220621 A1 * | 11/2004 | Zhou et al. | 607/2 |
| 2004/0230255 A1 | 11/2004 | Dobak, III | |
| 2005/0010250 A1 * | 1/2005 | Schuler et al. | 607/2 |
| 2005/0065574 A1 * | 3/2005 | Rezai | 607/45 |
| 2005/0143788 A1 | 6/2005 | Yun et al. | |
| 2005/0149146 A1 | 7/2005 | Boveja et al. | |
| 2005/0256028 A1 * | 11/2005 | Yun et al. | 514/2 |

FOREIGN PATENT DOCUMENTS

| | | | |
|---|---|---|---|
| WO | 00/61223 A1 | 10/2000 | |
| WO | 01/52932 A1 | 7/2001 | |
| WO | 01/58520 A1 | 8/2001 | |
| WO | 01/83028 A1 | 11/2001 | |
| WO | 02/04068 A1 | 1/2002 | |
| WO | 02/26315 A1 | 4/2002 | |
| WO | 02/26317 A1 | 4/2002 | |
| WO | 02/34331 A2 | 5/2002 | |
| WO | 02/43467 A2 | 6/2002 | |
| WO | 02/062291 A2 | 8/2002 | |

OTHER PUBLICATIONS

Grodin, et al., *Source of Estrogen Production in Postmenopausal Women*, JCE & M, 1973, vol. 36, No. 2, pp. 207-214.

Bloom, et al., *The Adrenal Contribution to the Neuroendocrine Responses to Splanchnic Nerve Stimulation in Conscious Calves*, Journal of Physiology (1988), 397, pp. 513-526.

Ahren, Bo "Sympathetic nerve Stimulation versus pancreatic norepinephrine Infusion in the Dog: 1) Effects on Basal Release of Insulin and Glucagon", Ndrocrinology vol. 121, No. 1 1986, (1987), pp. 323-331.

Accornero, Neri et al., "Selective Activation of Peripheral Nerve Fibre Groups of Different Diameter by Triangular Shaped Stimulus Pulses", J. Physiol., vol. 273,(1977), pp. 539-560.

Ahren, B. "Autonomic Reugulation of Islet Hormone Secretion—Implication for Health and Disease", Diabetologia, vol. 43,(2000), pp. 393-410.

Alamo, L et al., "Electrically-Evoked Catecholamine Release from Cat Adrenals", Biochemical Pharmacology, vol. 42, (1991), pp. 973-978.

Alvarez, Guy E., et al., "Sympathetic Neural Activation in Visceral Obesity", Circulation, (2002), pp. 2533-2536.

Andrews, Russell J., "Neuromodulation I. Techniques—Deep Brain Stimulation, Vagus Nerve Stimulation and Transcranial Magnetic Stimulation", Ann, N.Y. Acad. Sci., vol. 993,(2003), pp. 1-13.

Andrews, P. L., et al., "Interactions Between Splanchnic and Vagus Nerves in Control of Mean Intragastric Pressure in the Ferret", J. Physiol., vol. 351,(1984), pp. 473-490.

Ballard, Kathryn et al., "The Unresponsiveness of Lipid Metabolism in Canine Mesenteric Adipose Tissue to Biogenic Amines and to Sympathetic Nerve Stimulation", Acta Physiol. Scand., vol. 77,(1969), pp. 442-448.

Barone, Frank C., et al., "Gastric Distension Modulates Hypothalamic Neurons Via a Sympathetic Afferent Path Through the Mesencephalic Periaqueductal Gray", Brain Research Bulletin, vol. 38, No. 3,(1995), pp. 239-251.

Becker, James M., et al., "Myoelectric Control of Gastrointestinal and Biliary Motility: A Review", Surgery, vol. 89, No. 4,(1981), pp. 466-477.

Binks, A. P., et al., "High Strength Stimulation of the Vagus Nerve in Awake Humans: A Lack of Cardiorespiratory Effects", Respiration Physiology, vol. 127,(2001), pp. 125-133.

Birks, R. I., "Regulation by Patterned Preganglionic Neural Activity of Transmitter Stores in a Sympathetic Ganglion", J. Physiol., vol. 280,(1978), pp. 559-572.

Blackshaw, L. A., et al., "Vagal and Sympathetic Influences on the Ferret Lower Oesophagel Sphincter", Journal of the Autonomic Nervous System, vol. 66,(1997), pp. 179-188.

Bray, "Reciprocal Relation of Food Intakd and Sympathetic Activity: Experimental Observations and Clinical Implications", International Journal of Obesity, Suppl. 2; 24,(2000), pp. S8-S17.

Brown, Frederick D., et al., "Changes in Food Intake with Electrical Stimulation of the Ventromedial Hypothalamus in Dogs", J Neurosurgery, vol. 60,(1984), pp. 1253-1257.

Buckley, N. M., et al., "Circulatory Effects of Spanchnic Nerve Stimulation in Developing Swine", Am. J. Physiol, vol. 248,(1985), pp. H69-H74.

Bugbee, Martin et al., "Design of a Selective Nerve Stimulator", webpage, (1996).

Chen, Ke et al., "Induction of Leptin Resistance Through Direct Interaction of C-Reactive Protein with Leptin", Nature Medicine, vol. 12, No. 4,(2006), pp. 425-432.

Cigania, V. et al., "Gastric Peristalsis Control by Mono Situ Electrical Stimulation: a Preliminary Study", Obesity Surgery, vol. 6,(1996), pp. 247-249.

Cigaina, V. "Long-term Effects of Gastric Pacing to Reduce Feed Intake in Swine", Obesity Surgery, vol. 6,(1996), pp. 250-253.

Clutter, William E., "Epinephrine Plasma Metabolic Clearance Rates and Physiologic Thresholds for Metabolic and Hemodynamic Actions in Man", Journal of Clinic Investigations, vol. 66,(1980), pp. 94-101.

Crago, Patrick E., et al., "The Choice of Pulse Duration for Chronic Electrical Stimulation via Surface, Nerve and Intramuscular Electrodes", Annals of Biomedical Engineering, vol. 2,(1974), pp. 252-264.

Cummings, David E., et al., "Plasma Ghrelin Levels After Diet-Induced Weight Loss or Gastric Bypass Surgery", N. Engl J Med., vol. 346,(2002), pp. 1623-1630.

Cuschieri, A. et al., "Bilateral Endoscopic Splanchnicectomy Through a Posterior Thoracospic Approach", J. R. Coll. Surg. Edinb., vol. 39,(1994), pp. 44-47.

Delbro, D. et al., "Non-ganglionic Cholinergic Excitatory Pathways in the Sympathetic Supply to the Feline Stomach", Acta Physiol Scand, vol. 110,(1980), pp. 137-144.

Deloof, S. "Sympathetic Control of Antral and Pyloric Electrical Activity in the Rabbit", Journal of the Autonomic Nervous System, vol. 22,(1988), pp. 1-10.

Dodt, Christoph et al., "The Subcutaneous Lipolytic Response to Regional Neyral Stimulation is Reduced in Obese Women", Diabetes, vol. 49,(2000), pp. 1875-1879.

Dodt, Christoph et al., "Intraneural Stimulation Elicits and Increase in Subcuraneous Interstitial Glycerol Levels in Humans", J. Physiol., vol. 521.2,(1999), pp. 545-552.

Dodt, C. et al., "Sympathetic Control of White Adipose Tissue in Lean and Obese Humans", Acta Physiol Scand, vol. 177,(2003), pp. 351-357.

Dunning, Beth E., et al., "Pancreatic and Extrapancreatic Galanin Release During Sympathetic Neural Activation", Am. J. Physiol Endocrinal Metab, vol. 258,(1990), pp. 436-444.

Edwards, A. V., "Adrenal Catecholamine Output in Response to Stimulation of the Splanchnic Nerve in Bursts in the Conscious Calf", J. Physiol., vol. 327,(1982), pp. 409-419.

Edwards, A. V., et al., "The Effect of Splanchnic Nerve Stimulation on the Uptake of Atrial Natriuretic Peptide by the Adrenal Gland in Conscious Calves", J. Endocrinol Invest, vol. 13,(1990), pp. 887-892.

Edwards, A. V., et al., "The Effect of Splanchnic Nerve Stimulation on Adrenocortical Activity in Conscious Calves", J. Physiol, vol. 382,(1987), pp. 385-396.

Edwards, A. V., "The Glycogenolytic Response to Stimulatin of the Splanchnic Nerves in Adrenalectomized Calves, Sheep, Dogs, Cats and Pigs", J. Physiol., vol. 213,(1971), pp. 741-759.

Edwards, A. V., "The Sensitivity of the Hepatic Glycogenolytic Mechanism to Stimulations of the Splanchnic Nerves", J. Physiol., vol. 220,(1972), pp. 315-334.

Edwards, A. V., et al., "Adrenal Medullary Responses to Stimulation of the Splanchnic Nerve in the Conscious Calf", J. Physiol., vol. 308,(1980), pp. 15-27.

Engeland, William C., et al., "Splanchnic Nerve Stimulation Modulates Steroid Secretion in Hypophysectomized Dogs", Neuroendocrinology, vol. 50,(1989), pp. 124-131.

Fang, Zi-Ping et al., "Alternate Excitation of Large and Small Axons with Different Stimulations Waveforms: an Application to Muscle Activation", Med & Biol Eng & Comput, vol. 29,(1991), pp. 543-547.

Fredholm, B. B., et al., "Effects of Vasoactive Drugs on Circulation in Canine Subcutaneous Adipose Tissue", Acta Physiol Scand, vol. 79,(1970), pp. 564-574.

Friesen, et al., "The Effect of Preganglionic Stimulation on the Acetylcholine and Choline Content of a Sympathetic Ganglion", Canadian Journal of Physiology and Pharmacology, vol. 49, No. 5,(May 1971), pp. 375-381.

Fukushima, K. et al., "Differential Blocking of Motor Fibers by Direct Current", Pflugers Arch, vol. 358,(1975), pp. 235-242.

Furness, J. B., et al., "Effects of Vagal and Splanchnic Section on Food Intake, Weight, Serum Leptin and Hypothalamic Neuropeptide Y in Rat", Autonomic Neuroscience: Basic and Clinical, vol. 92,(2001), pp. 28-36.

Gy, Xu et al., "Modulation of Hypothalamic Arcuate Nucleus on Gastric Motility in Rats", World J Gastroenterol, vol. 4 (5),(1998), pp. 426-429.

Heck, Christi et al., "Vagus Nerve Stimulation Therapy, Epilepsy, and Device Parameters", Neurology, vol. 59 (Suppl. 4),(2002), pp. 31-37.

Holst, Jens J., et al., "Nervous Control of Pancreatic Exocrine Secretion in Pigs", Acta Physiol Scand, vol. 105, (1979), pp. 33-51.

Hopp, F. A., et al., "Effect of Anodal Blockade of Myelineated Fibers on Vagal C-fiber Afferents", Am. J. Physiol, vol. 239,(1980), pp. 454-462.

Itina, L. V., et al., "Impulsation of the Splanchnic and Vagus Nerves After Introduction of Fat Into the Lumen of the Small Intestine", Sechenov Physiological Journal of the USSR, (Russian Text with English Abstract),(1972).

Itina, L. V., et al., "Sympatho-Activatory and Sympatho-Inhibitory Afferent Fibers of Vagus and Splanchnic Nerves", Sechenov Physiological Journal of the USSR, Institute of Physiology Acad. Sci. Belorus, SSR, Minsk, (Russian Text with English Abstract),(1979).

Ito, Shigeo et al., "Gastric Vasodilator and Motor Responses to Splanchnic Stimulation and Tachykinins in the Dog", Gen. Pharmac., vol. 24,(1993), pp. 291-298.

Jarhult, Johannes et al., "The Functional Importance of Sympathetic Nerves to the Liver and Endocrine Pancreas", Ann. Surg., vol. 189, No. 1,(Jan. 1979), pp. 96-100.

Jaw, F.S. et al., "A Modified "Triangular Pulse" Stimulator for C-Fibers Stimulation", Journal of Neuorscience Methods, vol. 37,(1991), pp. 169-172.

Jonson, Claes et al., "Splanchnic Nerve Stimulation Inhibits Duodenal HCO3 Secretion in the Rat", American Physiological Society, (1988), pp. 709-712.

Jorum, E. et al., "Analgesia by Low-Frequency Nerve Stimulation Mediated by Low-Threshold Afferents in Rats", Pain, vol. 32,(1988), pp. 357-366.

Kaneto, Akio et al., "Effect of Splanchnic Nerve Stimulation on Glucagon and Insulin Output in the Dog", Endocrinology, vol. 96,(1975), pp. 143-150.

Katzeff, Harvey L., et al., "Metabolic Studies in Human Obesity During Overnutrition and Undernutrition: Thermogenic and Hormonal Responses to Norepinephrine", Metabolism, vol. 35, No. 2,(1986), pp. 166-175.

Koo, Betty et al., "Human Vagus Nerve Electrophhysiology", J Clin Neurophsiol, vol. 18(5),(Sep. 2001), pp. 429-433.

Kuo, David C., et al., "A Wide Field Electron Microscopic Analysis of the Fiber Constituents of the Major Splanchnic Nerve in Cat", The Journal of Comparative Neurology, vol. 210,(1982), pp. 49-58.

Kurose, Takeshi et al., "Mechanism of Sympathetic Neural Regulation of Insuling, Somatosatin and Glucagon Secretion", American Journal of Physiology, vol. 258,(1989), pp. 220-227.

Kurose, T. et al., "Glucagon, Insulin, and Somatostatin Secretion in Response to Sympathetic Neural Activation in Streptozotocin-Induce Diabetic Rats. A Study with the Isolated Perfused Rat Pancreas in Vitro", Diabetologia, vol. 35, (1992), pp. 1035-1041.

Leibel, Rudolph L., et al., "Changes in Energy Expenditure Resulting from Altered Body Weight", The New England Journal of Medicine, vol. 332 No. 10,(Mar. 1995), pp. 621-628.

Lerman, Sheldon H., et al., "Gastric Motor Response to Sympathetic Nerve Stimulation", Journal of Surgical Research, vol. 32,(1982), pp. 15-23.

Lerman, Sheldon H., et al., "Pyloric Motor Response to Sympathetic Nerve Stimulation in Dogs", Surgery, vol. 89 No. 4,(1981), pp. 460-465.

Lockard, Joan S., et al., "Feasibility and Safety and Vagal Stimulation in Monkey Model", Epilepsia, vol. 31 (Suppl.2),(1990), pp. 20-26.

Matthews, D. E., et al., "Effect of Epinephrine on Amino Acid and Energy Metabolism in Humans", American Journal of Physiology, vol. 258,(1990), pp. 948-956.

Mirkin, Bernard L., "Factors Influencing the Selective of Adrenal Medullary Hormones", Journal Pharmacol. Exp. Ther., vol. 132,(1960), pp. 218-225.

Monroe, Mary B., et al., "Direct Evidence for Tonic Sympathetic Support of Resting Metabolis Rate in Healthy Adult Humans", Am. J. Physiol. Endocrinol Metab., vol. 280,(2001), pp. 740-744.

Naidoo, N. et al., "Thoracic Splanchnic Nerves: Implications for Splanchnic Denervation", Journal of Anatomy, vol. 199,(2001), pp. 585-590.

Nakazato, Yoshikazu et al., "Gastric Motor and Inhibitor Response to Stimulation of the Sympathetic Nerve in the Dog", Jap. J. Pharmac, vol. 20,(1970), pp. 131-141.

Nakazato, Yoshikazu et al., "Atropine- and Hexamethonium-Resistant Motor Response to Greater Splanchnic Nerve Stimulation in the Dog Stomach", Journal of the Autonomic Nervous System, vol. 20,(1987), pp. 35-42.

Opsahl, Charles A., "Sympathetic Nervous System Involvement in the Lateral Hypothalamic Lesion Syndrome", Am. J. Physiol, vol. 232 (3),(1977), pp. 128-136.

Oro, Lars et al., "Influence of Electrical Supramedullary Stimulation on the Plasma Level of Free Fatty Acids, Blood Pressure and Heart Rate in the Dog", Acta Medica Scandinavica, vol. 178,(1965), pp. 697-711.

Pan, Hui-Lin et al., "Role of Summatino of Afferent Input in Cardiovascular Reflexes from Splanchnic Nerve Stimulation", Am. J. Physiol., vol. 270,(1996), pp. 849-856.

Peterson, Hugh R., et al., "Body Fat and the Activity of the Autonomic Nervous System", The New England Journal of Medicine, vol. 318 No. 17,(Apr. 1988), pp. 1077-1083.

Ratheiser, Klaus M., et al., "Epinephrine Produces a Prolonged Elevation in Metabolic Rate in Humans", Am. J. Clin. Nutr., vol. 68,(1998), pp. 1046-1052.

Ravussin, Eric "Reduced Rate of Energy Expenditure as a Risk Factor for Body-Weight Gain", New England Journal of Medicine, vol. 318,(1988), pp. 467-472.

Rosell, S. "Releast of Free Fatty Acids form Subcutaneous Adipose Tissue in Dogs Following Sympathetic Nerve Stimulation", Acta Physiol Scand., vol. 67,(1966), pp. 343-351.

Rozman, J. et al., "Multielectrode Spiral Cuff for Selective Stimulation of Nerve Fibres", Journal of Medical Engineering and Technology, vol. 16, No. 5,(1992), pp. 194-203.

Rozman, Janez et al., "Recording of Electroneurograms from the Nerves Innervating the Pancreas of a Dog", Journal of Neuroscience Methods, vol. 112,(2001), pp. 155-162.

Rozman, J. et al., "Recording of ENGs from the Nerves Innervating the Pancreas of a Dog During the Intraveneous Glucose Tolerance Test", Physiol. Meas., vol. 23(4),(2002), pp. 695-705.

Rozman, Janez et al., "Stimulation of Nerves Innervating the Dog's Pancreas", Artificial Organs, vol. 26(3),(2002), pp. 241-243.

Sato, T, et al., "Novel Therepeutic Stategy Against Central Baroreflex Failure: a Bionic Baroreflex System", National Library of Medicine, vol. 100(3),(1999), pp. 299-304.

Stoddard, Susan L., et al., "Adrenal Medullary Secretion with Splanchnic Stimulation in Spinal Cats", Journal of the Autonomic Nervous System, vol. 38,(1992), pp. 105-116.

Sweeney, James D., et al., "An Asymmetric Two Electrode Cuff for Generation of Unidirectionally Propagated Action Potentials", IEEE Transactions on Biomedical Engineering, vol. BME-33 No. 6,(Jun. 1986), pp. 541-549.

Shimazu, T. "Central Nervous System Regulation of Liver and Adipose Tissue Metabolism", Diabetologia, vol. 20, (1981), pp. 343-356.

Tataranni, P. "From Physiology to Neuroendocrinology: A Reappraisal of Risk Factors of Body Weight Gain in Humans", Diabetes and Metabolism, vol. 24 No. 2,(1998), pp. 108-115.

Terry, Reese et al., "An Implantable Neurocybernetic Prosthesis System", Epilepsia, vol. 31 Suppl. 2,(1990), pp. 33-37.

Thoren, Peter et al., "Anodal Block of Medullated Cardiopulmonary Vagal Afferents in Cats", J. Appl. Physiol., vol. 42(3),(1977), pp. 461-465.

Tran, M. A., et al., "Adrenergic Neurohumoral Influences on FFA Realese From Bone Marrow Adipose Tissue", J. Pharmacol, vol. 16 (2),(1985), pp. 171-179.

University of Florida, "Method & Apparatus for Allowing Selective Activity in Small Diameter Nerve Fibers", University of Florida Research and Graduate Programs.

Upton, Adrian R., et al., "Autonomic Stimulation", PACE, vol. 14,(Jan. 1991), pp. 50-69.

Van Den Honert, Christopher et al., "A Technique for Collision Block of Peripheral Nerve: Single Stimulus Analysis", IEEE Transactions on Biomedical Engineering, vol. BME-28 No. 5,(May 1981), pp. 373-378.

Wilkinson, Harold A., "Percutaneous Radiofrequency Upper Thoracic Sympathectomy", Neurosurgery, vol. 38, (1996), pp. 715-725.

Woodbury, Dixon M., et al., "Effects of Vagal Stimulation on Experimentally Induced Seizures in Rats", Epilepsia, vol. 31 (Suppl 2),(1990), pp. 7-19.

Hammond, et al., "Vagus Nerve Stimulation in Humans", Neurophysiological Studies and Electrophysiological Monitoring, Epilepsia, vol. 31, Suppl. 2., (1990), pp. S51-S59.

Mokdad, A "The Continuing Epidemics of Obesity and Diabetes in the United States", Journal of the American Medical Association, vol. 286, No. 10, (Sep. 2001), pp. 1195-1200.

Sjostrom, L "Epinephrine Sensitivity with respect to Metabolic Rate and Other Variables in Women", American Journal of Physiology, vol. 245., (Sep. 1982), pp. E431-E442.

Staten, M "Physiolotical Increments in Epinephrine Stimulate Metabolic Rate in Humans", American Journal of Physiology, vol. 253, (Nov. 1986), pp. E322-E330.

Strickland, T. "Performance of Local Anesthetic and Placebo Splanchnic Blocks via Indwelling Catheters to Predict Benefit from Thoracoscopic Splanchnicectomy in a Patient with Intractable Pancreatic Pain, Anesthesiology", (Apr. 1996), pp. 980-983.

Van, Den H., et al., "Generation of Unidirectionally Propagated Action Potentials in a Peripheral Nerve by Brief Stimuli, Science", vol. 206, (Dec. 14, 1979), pp. 1311-1312.

* cited by examiner

| Treatment Day | Frequency (HZ) | Pulse Width (usec) | Current (mA) | Duty Cycle (%) |
|---|---|---|---|---|
| 1 | 20 | 500 | 0.25 | 50 |
| 2 | 20 | 500 | 0.50 | 50 |
| 3 | 20 | 500 | 0.75 | 50 |
| 4 | 20 | 500 | 1.00 | 50 |
| 5 | 20 | 500 | 1.25 | 50 |
| 6 | 20 | 500 | 1.50 | 50 |
| 7 | 20 | 500 | 1.75 | 50 |
| 8 | 20 | 500 | 2.00 | 50 |
| 9 | 20 | 500 | 2.25 | 50 |
| 10 | 20 | 500 | 2.50 | 50 |
| 11 | 20 | 500 | 2.75 | 50 |
| 12 | 20 | 500 | 3.00 | 50 |
| 13 | 20 | 500 | 3.25 | 50 |
| 14 | 20 | 500 | 3.50 | 50 |
| 15 | 20 | 500 | 3.50 | 50 |
| 16 | 20 | 500 | 3.50 | 50 |
| 17 | 20 | 500 | 3.50 | 50 |
| 18 | 20 | 500 | 3.50 | 50 |
| 19 | 20 | 500 | 3.25 | 50 |
| 20 | 20 | 500 | 3.00 | 50 |
| 21 | 20 | 500 | 2.75 | 50 |
| 22 | 20 | 500 | 2.50 | 50 |
| 23 | 20 | 500 | 2.25 | 50 |
| 24 | 20 | 500 | 2.00 | 50 |
| 25 | 20 | 500 | 1.50 | 50 |
| 26 | 20 | 500 | 1.00 | 50 |
| 27 | 20 | 500 | 0.50 | 50 |
| 28 | 20 | 500 | 0.25 | 50 |

*FIG. 10*

| Treatment Day | Frequency (HZ) | Pulse Width (usec) | Current (mA) | Duty Cycle (%) |
|---|---|---|---|---|
| 1 | 20 | 500 | 0.25 | 50 |
| 2 | 20 | 500 | 0.50 | 50 |
| 3 | 20 | 500 | 0.75 | 50 |
| 4 | 20 | 500 | 1.00 | 50 |
| 5 | 20 | 500 | 1.50 | 50 |
| 6 | 20 | 500 | 2.00 | 50 |
| 7 | 20 | 500 | 2.75 | 50 |
| 8 | 20 | 500 | 3.50 | 50 |
| 9 | 20 | 500 | 3.50 | 50 |
| 10 | 20 | 500 | 3.50 | 50 |
| 11 | 20 | 500 | 3.50 | 50 |
| 12 | 20 | 500 | 3.50 | 50 |
| 13 | 20 | 500 | 3.50 | 50 |
| 14 | 20 | 500 | 3.50 | 50 |
| 15 | 20 | 500 | 3.50 | 50 |
| 16 | 20 | 500 | 3.50 | 50 |
| 17 | 20 | 500 | 3.50 | 50 |
| 18 | 20 | 500 | 3.50 | 50 |
| 19 | 20 | 500 | 3.50 | 50 |
| 20 | 20 | 500 | 3.50 | 50 |
| 21 | 20 | 500 | 3.50 | 50 |
| 22 | 20 | 500 | 3.50 | 50 |
| 23 | 20 | 500 | 3.50 | 50 |
| 24 | 20 | 500 | 3.50 | 50 |
| 25 | 20 | 500 | 3.00 | 50 |
| 26 | 20 | 500 | 2.00 | 50 |
| 27 | 20 | 500 | 1.00 | 50 |
| 28 | 20 | 500 | 0.50 | 50 |

FIG. 11

DEVICES AND METHODS FOR GYNECOLOGIC HORMONE MODULATION IN MAMMALS

CROSS-REFERENCE TO RELATED APPLICATIONS

This application claims priority under 35 U.S.C. section 119(e) from U.S. Provisional Patent Application Ser. No. 60/605,779, filed Aug. 31, 2004, titled "Neurostimulation for Gynecology," the contents of which are incorporated by reference herein in their entirety.

BACKGROUND OF THE INVENTION

1. Field of the Invention

The invention relates generally to the field of stimulating nerves to treat a patient. More specifically, the invention relates to methods and devices for electrically stimulating nerves to control hormone levels in a female mammal.

2. Description of the Related Art

The secretion and reception of hormones by the various tissues of mammalian bodies is known to control a wide variety of body functions. Manipulation of hormone levels in mammals has been used widely to achieve a variety of desired results including the treatment of medical conditions and the inducement of various effects, such as the simulation of hormonal levels of pregnancy for birth control and the simulation of normal reproductive hormone levels for the treatment of menopause in females. One current method for treating peri- and post-menopausal women has been hormone replacement therapy (HRT), the systemic administration of exogenous hormones including estrogen alone or estrogen in combination with progesterone. However, HRT has been associated with significant side effects in some cases such as increased incidence of various forms of cancer and osteoporosis. In addition, the absence of therapy may also result in various forms of cancer, osteoporosis, and many other well documented side effects. A discussion of examples of some of these treatments and side effects can be found in a chapter entitled Reproductive Endocrinology by S. Yen and R. Jaffe in Physiology, Pathophysiology and Clinical Management, 2d Edition, WB Saunders Company, 1986 (Yen).

One current method of birth control is the exogenous systemic administration of estrogen and/or progesterone in the form of the birth control pill. A similar treatment may also be administered in newer embodiments that include a semi-permanent implant such as the Norplant® or a controlled hormone-releasing patch that is applied to the skin of a patient. The administrative modality of these latest products are indicative of the problem of patient compliance of consistently taking the medication for effective birth control, Compliance issues are minimized but not eliminated by the newer implant and patch modalities because patches and implants still require compliance. What has been needed is an adaptable modality of hormone modulation, specifically, reproductive hormone modulation, that addresses these and other concerns. What has also been needed is a modality of hormone modulation for birth control that reduces the need for patient compliance. Further, what has been needed is a modality for hormone modulation for the treatment of menopause and its associated symptoms that reduces or eliminates the side effects associated with known treatment modalities.

SUMMARY OF THE INVENTION

In one embodiment, a method of treating gynecological conditions in a body of a mammal includes stimulating tissue at a first stimulation energy dose to induce the production of at least one gynecologic hormone, measuring the concentration of the at least one gynecologic hormone in the body of the mammal and comparing the measured concentration of the at least one gynecologic hormone against a desired reference concentration. Thereafter, the stimulation energy dose is adjusted according to any measured difference in concentration between the reference concentration and the measured concentration of the at least one gynecologic hormone and tissue stimulated at the adjusted stimulation energy dose.

In another embodiment, a method of treating menopause including the periods known as pre-menopause, peri-menopause and post-menopause to prevent or reduce the severity of medical conditions and side effects associated with all phases of menopause includes surgically implanting a tissue stimulation device in the body of a patient that provides electrical stimulation with stimulation parameters that are controllable and repeatable. Tissue of the patient's body is then electrically stimulated with tissue stimulation energy from the tissue stimulation device according to a tissue stimulation pattern that induces a desired hormone level pattern.

In another embodiment, a method of interrupting the normal estrus cycle in a mammal and altering the hormone production related to the estrus cycle to prevent pregnancy, includes electrical stimulation of tissue of the body of the mammal. This embodiment may also include surgically implanting a tissue stimulation device that provides electrical stimulation with stimulation parameters that are controllable and repeatable. Thereafter, tissue of the mammal is electrically stimulated with tissue stimulation energy from the tissue stimulation device according to a tissue stimulation pattern that induces a desired hormone level pattern.

In another embodiment, a tissue stimulation device for treatment of gynecological conditions in a patient, includes an electrical tissue stimulation energy source including a logic and control unit coupled to a memory unit that stores machine readable information. The machine readable information may be read by the logic and control unit to produce a tissue stimulation pattern that induces a desired hormone level pattern for gynecologic hormones. An electrode is in electrical communication with the electrical tissue stimulation energy source and is configured to be coupled to a nerve of the patient.

In some embodiments, the invention includes methods of treating gynecological conditions in a body of a mammal by stimulating tissue at a first stimulation energy dose to induce the production of at least one gynecologic hormone; measuring the concentration of the at least one gynecologic hormone in the body of the mammal; comparing the measured concentration of the at least one gynecologic hormone against a desired reference concentration; and adjusting the stimulation energy dose according to any measured difference in concentration between the reference concentration and the measured concentration of the at least one gynecologic hormone; and stimulating tissue at the adjusted stimulation energy dose. In some embodiments of the method, the step of stimulating tissue is performed by a tissue stimulation device comprising a memory unit with machine readable information representing a desired hormone level pattern and wherein comparing the measured concentration of the at least one gynecologic hormone against a desired reference concentration comprises comparing the measured concentration against the desired hormone level pattern. In some embodiments of the method, the desired hormone level pattern comprises a pre-menstrual hormone level pattern for a human female.

In some embodiments, the invention includes a method of treating gynecological conditions in a mammal, comprising electrical stimulation of hormone producing organs to induce a predetermined gynecologic hormone level pattern. In some embodiments of the method, the gynecological condition being treated comprises menopause and wherein the predetermined gynecologic hormone level pattern comprises substantially the gynecologic hormone level pattern of a pre-menopausal mammal. In some embodiments, the method further comprises surgically implanting a programmable electrical tissue stimulation energy source that provides electrical stimulation with stimulation parameters that are controllable and repeatable; and electrically stimulating tissues according to predetermined tissue stimulation patterns that induce the production of gynecologic hormones according to a predetermined pattern of hormone production. In some embodiments of the method, the mammal is a human. In some embodiments of the method, the electrical stimulation follows a tissue stimulation pattern configured to induce the production of a pattern of hormone levels corresponding to a typical estrus cycle pattern of hormone levels. In some embodiments the typical estrus cycle and pattern of hormone levels is about 26 to about 30 days in duration. In other embodiments the tissue stimulation pattern corresponds to an endogenous pattern of hormone levels and hormone production for a normal 28-day estrus cycle.

In some embodiments of the method, the inducement of the predetermined gynecologic hormone level pattern comprises the inducement of the production of at least one hormone selected from the group consisting of estrogen, progesterone, estradiol, pregnenolone, androstenedione, estrone, androgens, and progestins.

In some embodiments of the methods described above, the tissue stimulation pattern comprises: increasing the electrical dose from about day 1 to about day 14; holding the electrical dose substantially constant from about day 15 to about day 18; and decreasing the electrical dose from about day 19 to about day 28. In some embodiments of the method, those steps are repeated at least once.

In other embodiments of the invention, the tissue stimulation pattern comprises: increasing the electrical dose from about day 1 to about day 7; holding the electrical dose substantially constant from about day 8 to about day 24; and decreasing the electrical dose from about day 25 to about day 28. In some embodiments of the method, those steps are repeated at least once.

In some embodiments of the invention, the tissue stimulation pattern comprises: increasing the electrical dose from about day 1 to about day 7; holding the electrical dose substantially constant from about day 8 to about day 28; and continuing to hold the electrical dose substantially constant beyond day 28. In some embodiments of the methods described above, the method includes holding the electrical dose substantially constant until treatment is terminated.

Some embodiments of the invention include a method of treating menopause including the periods known as pre-menopause, peri-menopause and post-menopause to prevent or reduce the severity of medical conditions and side effects associated with all phases of menopause, comprising: surgically implanting a tissue stimulation device that provides electrical stimulation with stimulation parameters that are controllable and repeatable; and electrically stimulating tissue with tissue stimulation energy from the tissue stimulation device according to a tissue stimulation pattern that induces a desired hormone level pattern. In some embodiments of the methods described above, the frequency of the tissue stimulation energy is from about 1 Hz and about 50 Hz. In some embodiments of the methods described above, the mammal comprises a human. In some embodiments of the methods the hormone level pattern induced by the tissue stimulation pattern corresponds to a hormone level pattern of a typical estrus cycle. In some embodiments, the typical estrus cycle and tissue stimulation pattern are about 26 days to about 30 days in duration. In some embodiments of the method the tissue stimulation pattern induces a hormone production pattern corresponding to a normal hormone production pattern for a typical estrus cycle. In some embodiments of the methods least one of the hormones comprising the hormone production pattern is selected from the group consisting of estrogen, progesterone, estradiol, pregnenolone, androstenedione, estrone, androgens, and progestins.

In some embodiments of the methods, the tissue stimulation pattern comprises: increasing the electrical dose from about day 1 to about day 14; holding the electrical dose constant from about day 15 to about day 18; and decreasing the electrical dose from about day 19 to about day 28. In some embodiments, the methods further comprise repeating those steps at least once.

In other embodiments, the tissue stimulation pattern comprises: increasing the electrical dose from about day 1 to about day 7; holding the electrical dose constant from about day 8 to about day 24; and decreasing the electrical dose from about day 25 to about day 28. In some embodiments, the method further comprises repeating those steps at least once. In some embodiments of the methods the tissue stimulation pattern comprises: increasing the electrical dose from about day 1 to about day 7; holding the electrical dose substantially constant from about day 8 to about day 28; and continuing to hold the electrical dose substantially constant beyond day 28. In some embodiments the methods further comprises continuing to hold the electrical dose substantially constant until treatment is terminated.

Some embodiments of the invention include a method of interrupting the normal estrus cycle in a mammal and altering the hormone production related to the estrus cycle to prevent pregnancy, comprising, electrical stimulation of tissue of the body of the mammal. In some embodiments the methods further comprise: surgically implanting a tissue stimulation device that provides electrical stimulation with stimulation parameters that are controllable and repeatable; and electrically stimulating tissue with tissue stimulation energy from the tissue stimulation device according to a tissue stimulation pattern that induces a desired hormone level pattern.

In some embodiments of the methods the hormone level pattern induced by the tissue stimulation pattern corresponds to a hormone level pattern of a typical estrus cycle. In some embodiments of the methods the typical estrus cycle and tissue stimulation pattern are about 26 days to about 30 days in duration. In some embodiments of the methods the tissue stimulation pattern induces a hormone production pattern corresponding to a normal hormone production pattern for a typical estrus cycle. In some embodiments of the methods at least one of the hormones comprising the hormone production pattern is selected from the group consisting of estrogen, progesterone, estradiol, pregnenolone, androstenedione, estrone, androgens, and progestins.

In some embodiments of the methods the tissue stimulation pattern comprises increasing the electrical dose from about day 1 to about day 14; holding the electrical dose constant from about day 15 to about day 18; and decreasing the electrical dose from about day 19 to about day 28. The method of claim 37 further comprising repeating (a) through (c) at least once.

In some embodiments of the methods the tissue stimulation pattern comprises increasing the electrical dose from about day 1 to about day 7; holding the electrical dose constant from about day 8 to about day 24; and decreasing the electrical dose from about day 25 to about day 28. In some embodiments the methods further comprise repeating (a) through (c) at least once.

In some embodiments of the methods the tissue stimulation pattern comprises: increasing the electrical dose from about day 1 to about day 7; holding the electrical dose substantially constant from about day 8 to about day 28; and continuing to hold the electrical dose substantially constant beyond day 28. In some embodiments the methods further comprise continuing to hold the electrical dose substantially constant until treatment is terminated.

In some embodiments of the methods the estrus is interrupted without raising the baseline mean arterial pressure of the mammal by more than 25%. In some embodiments of the methods the estrus is interrupted without raising the baseline heart rate of the mammal by more than 25%.

Some embodiments of the invention include a method of treating multiple gynecology conditions in a mammal, comprising, electrically stimulating tissues with multiple tissue stimulation patterns so as to alter the hormone production. In some embodiments of the methods the gynecological conditions comprise interruption of the estrus cycle and treatment of menopause and wherein the gynecological conditions are treated separately and sequentially. In some embodiments of the methods the gynecological conditions comprise interruption of the estrus cycle to prevent pregnancy, resumption of normal estrus through interruption of electrical tissue stimulation to allow a resumption of a normal estrus cycle and conception, interruption of the estrus cycle a second time to prevent pregnancy and treatment of menopause by changing the tissue stimulation pattern.

Some embodiments of the invention include a tissue stimulation device for treatment of gynecological conditions in a patient, comprising: an electrical tissue stimulation energy source including a logic and control unit coupled to a memory unit that stores machine readable information read by the logic and control unit to produce a tissue stimulation pattern that induces a desired hormone level pattern for gynecologic hormones; and an electrode in electrical communication with the electrical tissue stimulation energy source and configured to be coupled to a nerve of the patient. In some embodiments the devices further comprise a battery in electrical communication with the logic and control unit. In some embodiments the logic and control unit further comprises a data input channel for input of hormone concentration measurement data and a feedback loop configured to adjust an electrical dose of the tissue stimulation pattern according to the hormone concentration measurement data. In some embodiments of the devices the data input channel comprises an antenna. In some embodiments of the devices the tissue stimulation energy source comprises an IPG. In some embodiments of the devices the hormone level pattern induced by the tissue stimulation pattern corresponds to a hormone level pattern of a typical estrus cycle. In some embodiments of the devices the typical estrus cycle and tissue stimulation pattern are about 26 days to about 30 days in duration. In some embodiments of the devices tissue stimulation pattern induces a hormone production pattern corresponding to a normal hormone production pattern for a typical estrus cycle. In some embodiments of the devices at least one of the hormones comprising the hormone production pattern is selected from the group consisting of estrogen, progesterone, estradiol, pregnenolone, androstenedione, estrone, androgens, and progestins.

In some embodiments of the devices the tissue stimulation pattern comprises increasing the electrical dose from about day 1 to about day 14; holding the electrical dose constant from about day 15 to about day 18; and decreasing the electrical dose from about day 19 to about day 28. In some embodiments of the devices the tissue stimulation pattern further comprises repeating (a) through (c) at least once. In other embodiments of the devices the tissue stimulation pattern comprises increasing the electrical dose from about day 1 to about day 7; holding me electrical dose constant from about day 6 to about day 24; and decreasing the electrical dose from about day 25 to about day 28. In some embodiments of the devices the tissue stimulation pattern further comprises repeating (a) through (c) at least once.

In some embodiments of the devices the tissue stimulation pattern comprises increasing the electrical dose from about day 1 to about day 7; holding the electrical dose substantially constant from about day 8 to about day 28; and continuing to hold the electrical dose substantially constant beyond day 28. In some embodiments of the devices the tissue stimulation pattern further comprises continuing to hold the electrical dose substantially constant until treatment is terminated.

These features of the embodiments will become more apparent from the following detailed description when taken in conjunction with the accompanying exemplary drawings.

BRIEF DESCRIPTION OF THE DRAWINGS

FIG. 10 shows a table of tissue stimulation parameters for a dynamic tissue stimulation pattern configured to produce a hormone level pattern for treatment of menopause.

FIG. 11 shows a table of tissue stimulation parameters for a substantially static tissue stimulation pattern configured to produce a hormone level pattern for treatment of menopause.

DETAILED DESCRIPTION OF THE PREFERRED EMBODIMENT

Figure 1:
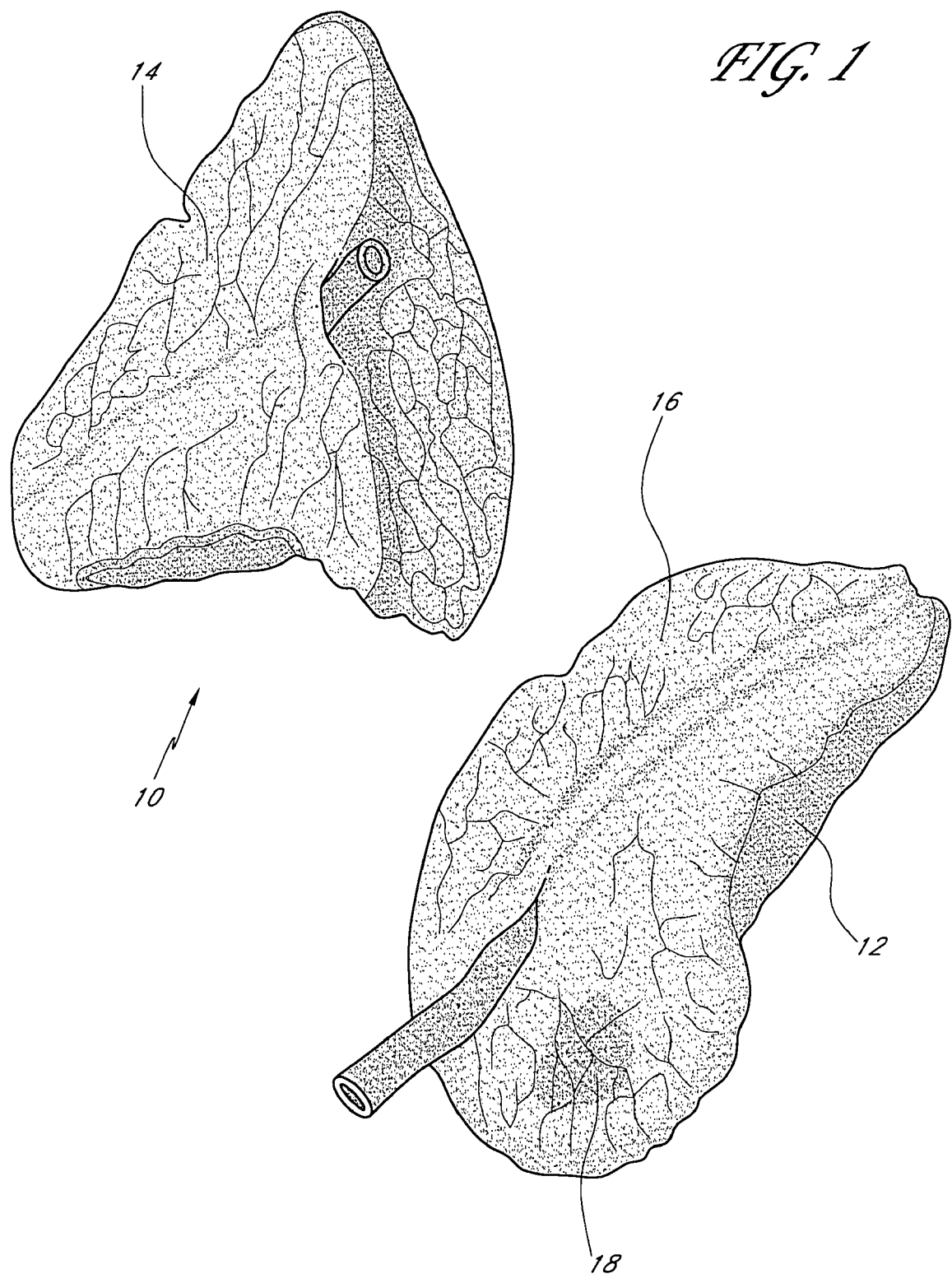
FIG. 1 is an exploded perspective view of a human adrenal gland.

The functioning of a gynecological system of a mammal is inextricably intertwined with the production and circulation of hormones within the body of the mammal. Normal function of estrus, pregnancy, menopause, etc., is dependent on the presence and concentration levels of circulating hormones such as estrogen, progesterone, estradiol, pregnenolone, androstenedione, estrone, androgens or progestins and their precursors.

Stimulation of neurological tissues that innervate organs associated with hormone production and regulation or direct stimulation of said organs associated with hormone production and regulation is presented as a method of treating gynecological conditions. Embodiments of the invention relate to the modulation of the hormones responsible for symptoms associated with gynecological conditions. Pre-, peri- and post-menopause (PPM) hormone production is one such gynecological condition. The same modulation, with different stimulation patterns, can be used as a form of birth control. More specifically, embodiments of the invention are directed to the permanent implantation of a tissue stimulation device or devices that may include an electrical stimulator with machine readable information stored therein such as application-specific software, electrical leads, and an electrode or electrodes to electrically stimulate the organs and tissues responsible for the production of the hormones related to gynecological conditions such as estrogen and progesterone and their precursors. Examples of such gynecological conditions include PPM and birth control.

Electrical stimulation is presented herein as an exemplary embodiment of tissue stimulation energy, however, other modalities of stimulation may be used to achieve the same or similar results. Stimulation of tissue by energy sources or energy types such as radio frequency, ultrasound, microwaves, lasers, masers, non-coherent light energy, nuclear, etc. is contemplated. In addition, direct or indirect stimulation of tissue by other modalities such as pharmacological stimulation is also contemplated.

The use of electrical stimulation of nerves to treat various maladies such as epilepsy, pain management, and depression is well documented. These technologies involve the surgical implantation, either via an open surgical procedure or a laparoscopic or thoracoscopic procedure, of an electrode with an associated wire lead and an implantable pulse generator (IPG). The electrode can take one of many forms such as a needle electrode or a cuff electrode. In addition, electrical stimulation of peripheral nerves has demonstrated the ability to cause the production (up-regulation) or elimination of production (down-regulation) of various hormones such as ghrelin, etc. As such, in some embodiments a permanent implantable electrical generator with application-specific software and associated leads and electrodes offer a potential means to achieve such hormonal regulation for treatment of gynecological conditions or effects.

For such embodiments, an electrode may be placed via an endoscopic procedure, which may be a laparoscopic or thoracoscopic procedure, to a peripheral nerve of a patient that innervates the organs and/or tissues associated with hormone up-regulation and down-regulation related to PPM and birth control. Desired patterns of electrical stimulation may be varied or otherwise used to modulate hormone levels. Such modulation may be used to create the normal cyclical pattern of hormone production patterns for hormones related to gynecological conditions for the treatment of menopause and birth control in a female mammal, and for some embodiments, specifically for a human female. Such hormone production patterns and hormone level patterns have been well documented.

Hormone regulation by stimulation of peripheral nerves and other tissues may be better tolerated than systemic administration of exogenous hormones because the up-regulation/down-regulation occurs locally, more akin to the natural process of hormone regulation. By using electrical stimulation of peripheral nerves, the hormones and their precursors are produced endogenously. The production of precursors such androstenedione and pregnenolone may also be beneficial compared to administration of hormones such as estrogen and progesterone. In addition to efferent effects related to end organs, an afferent effect (signal sent back up to the brain, specifically the hypothalamus) may also contribute to the stimulation of the modulation of the production of hormones of interest which may include estrogen, progesterone, estradiol, pregnenolone, androstenedione, estrone, androgens and progestins and their precursors as well as others.

During the PPM periods, a woman experiences significant decreases in the production of plasma estrogen and progesterone, and their precursors. The ovaries, ovum and follicles are significant sources of estrogen in pre-menopausal women. With the decreased ovulation associated with the peri- and post-menopause condition in older women and other mammals an associated decrease in the production of estrogen and progesterone and their precursors are observed. Another significant source of estrogen and progesterone and their precursors in pre-menopausal women is the adrenal cortex. It has been shown that in the post-menopausal woman, about 70% of androstenedione, which is a precursor to estrogen, is secreted by the adrenal cortex.

While there is some controversy around the source of estrogen and androgens, such as androstenedione, in the post-menopausal woman, the production of androgens, particularly androstenedione, in the adrenal cortex has been observed as discussed in a publication entitled Source of estrogen production in post menopausal women, by J. M. Grodin, P. K. Siiteri and P. C. MacDonald in J Clin Endocrinol Metab, 36:207, 1973. While production of these precursors occurs in the adrenal cortex, the conversion from precursor to estrogen may occur elsewhere such as in visceral fat, liver, kidney and the hypothalamus. Adrenal cortex plasma cholesterol has been reported to be a precursor to progesterone by E. Botte, S. Coudert and Y. Lepebose in an article entitled Steroid production from plasma cholesterol: In vivo conversion of plasma cholesterol to ovarian progesterone and adrenal C19 and C21 steroids in Humans in J Clin Endocrinol Metab 38:394, 1974. Adrenocorticotropic hormone (ACTH) produced in the adrenal cortex accelerates the conversion of cholesterol to pregnenolone in the adrenal cortex and pregnenolone is a precursor of progesterone.

As such, the adrenal cortex is one desired site for electrical stimulation to cause the production of estrogen, progesterone and their precursors such as estradiol, androstenedione and pregnenolone. An example of a human adrenal gland 10 is shown in FIG. 1. The adrenal gland 10 is comprised of a central medulla and a surrounding tissue cortex 12. The view of FIG. 1 shows the hepatic area 14, the gastric area 16 and the pancreatic area 18. The adrenal cortex 12 makes up approximately 90% of the adrenal gland 10. The adrenal cortex 12 is innervated mostly by the vagus nerve, and to a lesser extent, by the splanchnic nerve, while the adrenal medulla is innervated mostly by the greater splanchnic nerve with minor vagus nerve innervation. Some embodiments include a method of electrically stimulating any portion of the vagus nerve including peripheral, thoracic and/or abdominal, vagus nerve(s) to cause the up- and/or down-regulation of hormones related to gynecology, menopause and or estrus. Other embodiments include a method of electrically stimulating any portion of the splanchnic nerve including the peripheral, thoracic and/or abdominal, greater splanchnic, lesser splanchnic or least splanchnic nerve(s) to cause the up- and/or down-regulation of hormones related to gynecology, menopause and or estrus.

Figure 2:
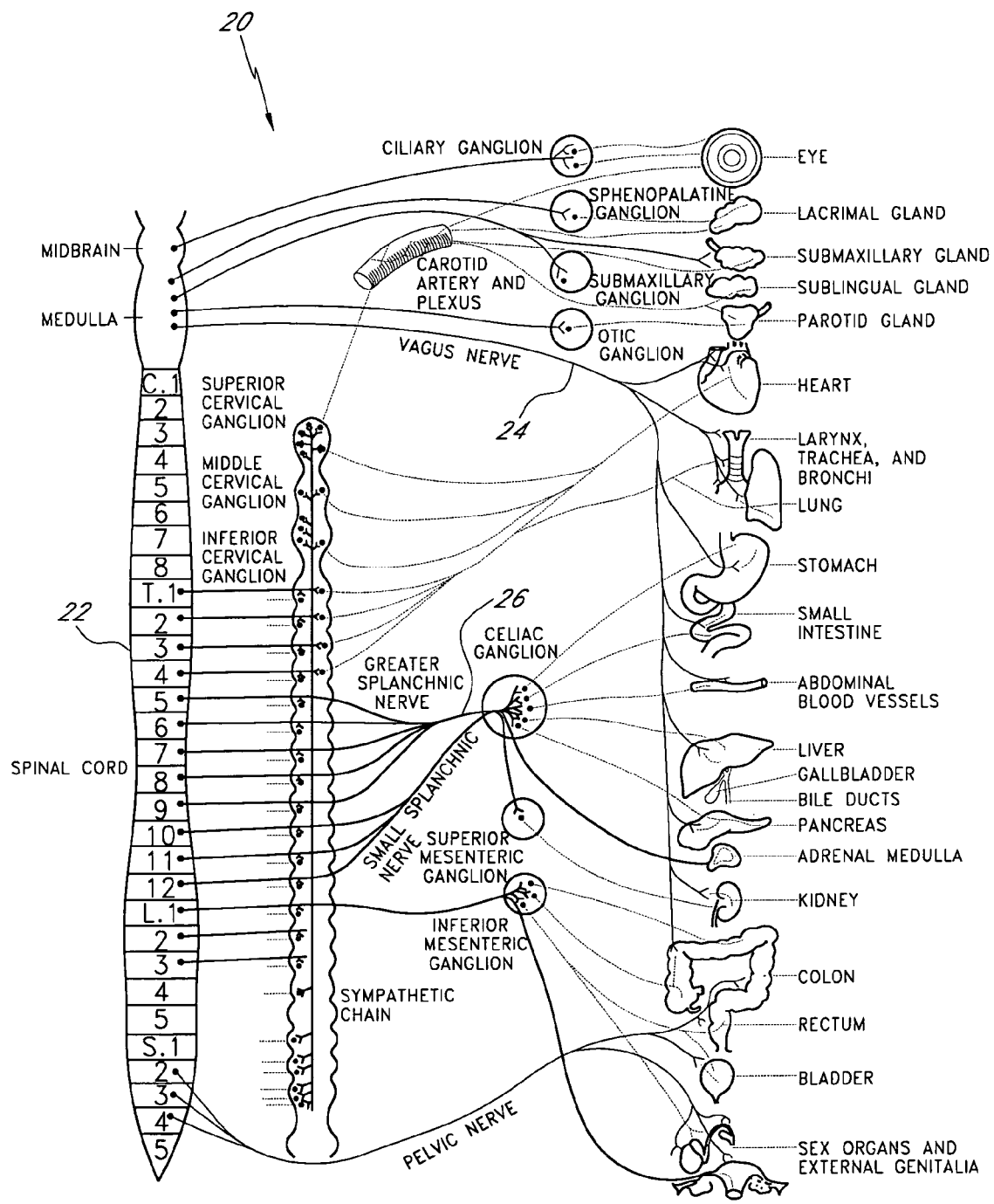
FIG. 2 is a diagram of a human efferent autonomic nervous system.

FIG. 2 shows a diagram of a human efferent autonomic nervous system 20. The autonomic nervous system 20 is a subsystem of the human nervous system that controls involuntary actions of smooth muscle tissue including blood vessels, the digestive system, the heart and various glands. The autonomic nervous system 20 includes the sympathetic nervous system and the parasympathetic nervous system. The hypothalamus (not shown) generally controls the sympathetic nervous system via descending neurons in the ventral horn of the spinal cord 22. These descending neurons synapse with preganglionic sympathetic neurons that exit the spinal cord and form the white communicating ramus. The preganglionic neuron will either synapse in a peripheral or collateral ganglion. After synapsing in a particular ganglion, a postsynaptic neuron continues on to innervate the organs of the body including the heart, liver, pancreas, intestines etc. A postsynaptic neuron may also innervate the adipose tissue and glands of the periphery and the skin. To stimulate the production of the desired hormones, electrical stimulation of the lower thoracic and/or upper abdominal vagus nerve 24 will in turn stimulate the adrenal cortex 12 to produce hormones and hormone precursors in order to produce a desired effect. The same effect may be possible with the electrical stimulation of the greater splanchnic nerve 26. Directly stimulating the adrenal gland 10 may also be performed in order to modulate hormone production, as may the direct stimulation of the ovarian nerve (not shown).

Figure 3:
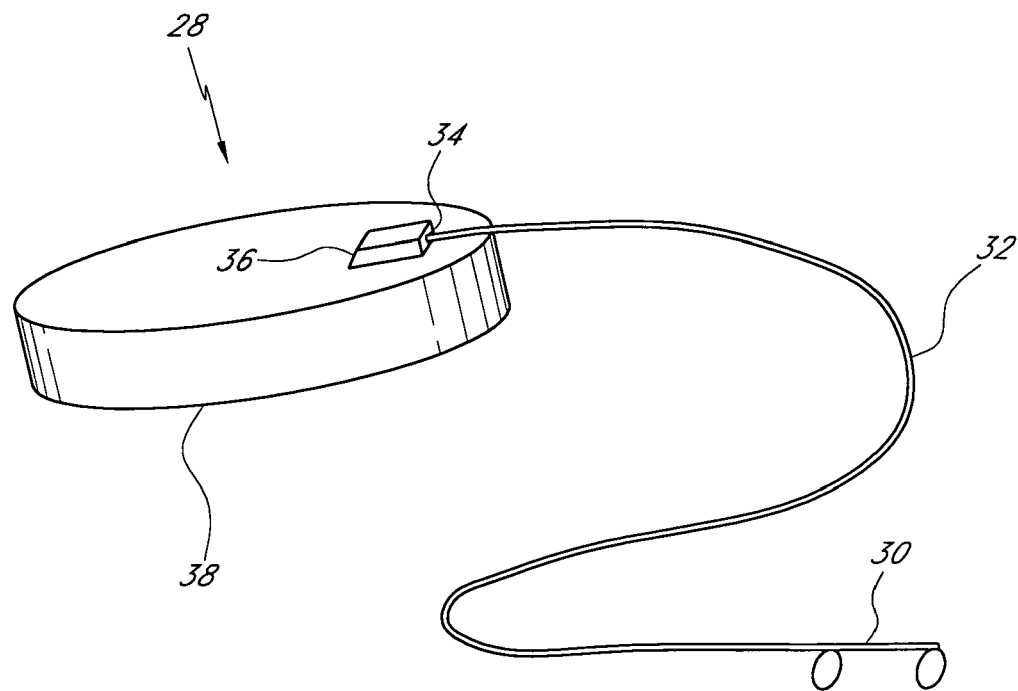
FIG. 3 is a perspective view of an embodiment of an electric tissue stimulation device including an implantable pulse generator electrically coupled to a cuff electrode by an elongate electric lead.

In order to produce a desired stimulation pattern for gynecologic hormone regulation, a variety of devices and methods may be used. FIGS. 3-6 illustrate an embodiment of a programmable source of tissue stimulation in the form of an electrical tissue stimulation device that may be used for some embodiments of hormone modulation. Referring to FIG. 3, an implantable pulse generator (IPG) 28 is coupled to a cuff electrode 30 by a conductive lead 32. Embodiments of the conductive lead 32 may include a central conductor or bundle of central conductors, braided or otherwise, surrounded by an insulation layer. The conductive lead 32 may generally be a flexible thin member capable of transmitting electrical energy of a variety of types and may be electrically insulated and shielded in order to prevent energy from escaping into surrounding tissue. The conductive lead 32 may be configured to transmit direct current, alternating current including radiofrequency current and the like. The length of embodiments of the conductive lead 32 may be from about 10 cm to about 100 cm. Pins at a proximal end 34 of the electrode lead 32 plug into a receptacle 36 in the IPG 28. The various circuitry components of the IPG 28 may be housed in an epoxy-titanium shell 38. The IPG shell 38 is generally disc shaped and may have an outer transverse dimension of about 3 cm to about 15 cm and a thickness of about 3 mm to about 15 mm.

Figure 4:
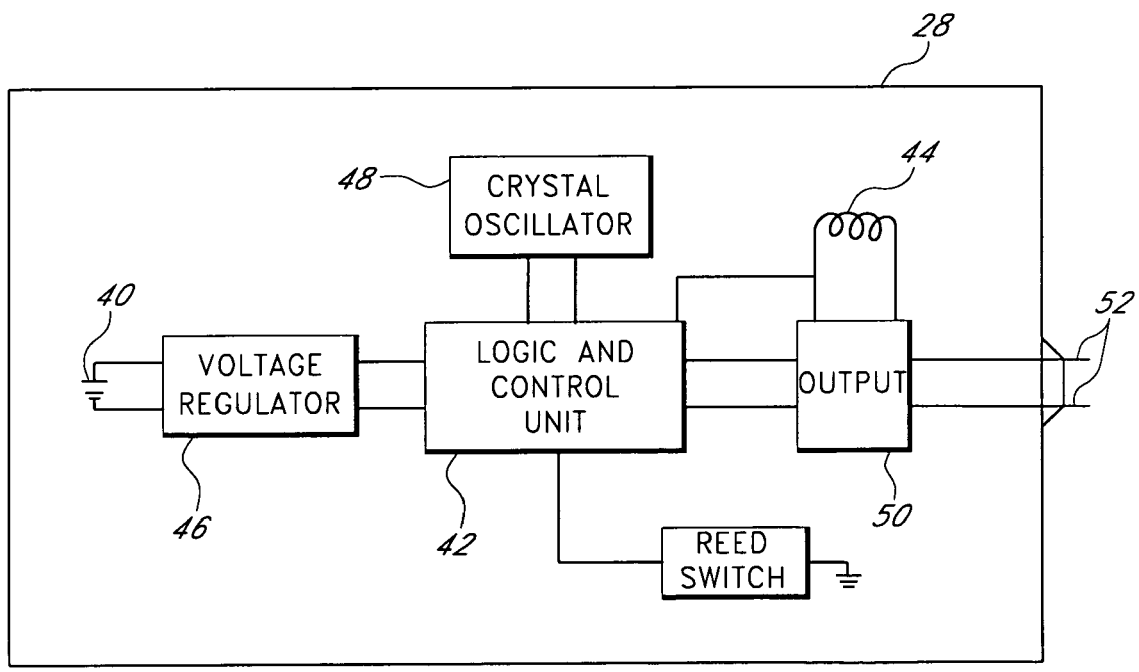
FIG. 4 shows a schematic view of an embodiment of an implantable pulse generator.

Referring to the schematic representation of an embodiment of an IPG 28 in FIG. 4, the IPG 28 contains a battery 40 that is coupled to and supplies power to a logic and control unit 42 that may include a central processing unit and memory unit (not shown). The battery 40 itself may be of a rechargeable variety that may be recharged either by direct electric coupling with a recharge voltage supply or by remote inductive coupling. If inductive coupling is to be used, a recharge signal may be generated external to a patient's body and coupled to a receiver which is in turn in electrical communication with the battery 40. A tissue stimulation pattern, which, for some embodiments, may be a tissue stimulation or treatment algorithm, may be programmed into the memory unit of the logic and control circuit 42. The memory unit may include software or hardware that is configured to store information necessary to carry out a tissue stimulation pattern or regimen in a repeatable and controllable manner. Such information stored in the memory unit may be uploaded or downloaded via non-invasive wireless communication via an antenna 44 which is coupled to the logic and control unit 42.

A voltage regulator 46 is disposed between the battery 40 and logic and control unit 42 and controls the battery output to the logic and control unit 42. A crystal oscillator 48 provides timing signals for output pulse signals and for the logic and control unit 42 generally. The antenna 44 is coupled to an output unit 50 and the logic and control unit 42 and is used for transmitting information to and receiving communications from an external programmer or wand (not shown). The external programmer or wand can also check on the status of the IPG 28. The output unit 50 is coupled to the electric lead 32 of the IPG 28 which may terminate at a receptacle 52 configured to couple electrically with the pins on the proximal end 34 of the conductive lead 32 of the cuff electrode 30. The output unit 50 may also include a radio transmitter to inductively couple with a wireless electrode embodiment (not shown) of the cuff electrode 30. For such an embodiment, conductive electric leads between the IPG 28 and the cuff electrode 30 would be unnecessary.

The logic and control unit 42 controls the tissue stimulation output energy and includes a memory unit that may store machine readable information which allows for programming of desired tissue stimulation patterns including the chronological profile of electrical stimulation energy parameters over time including the signal voltage, frequency, pulse width, duty cycle and the like. Such desired tissue stimulation patterns may be configured to induce desired hormone production patterns necessary to simulate or produce desired hormone level patterns. Some of the desired hormone level pattern embodiments may have a duration of about 25 days to about 35 days and encompass at least one menstrual cycle of a patient. One embodiment of the IPG 28 may include the Cyberonics Model 101 manufactured by the Cyberonics Company in Houston, Tex.

Figure 5:
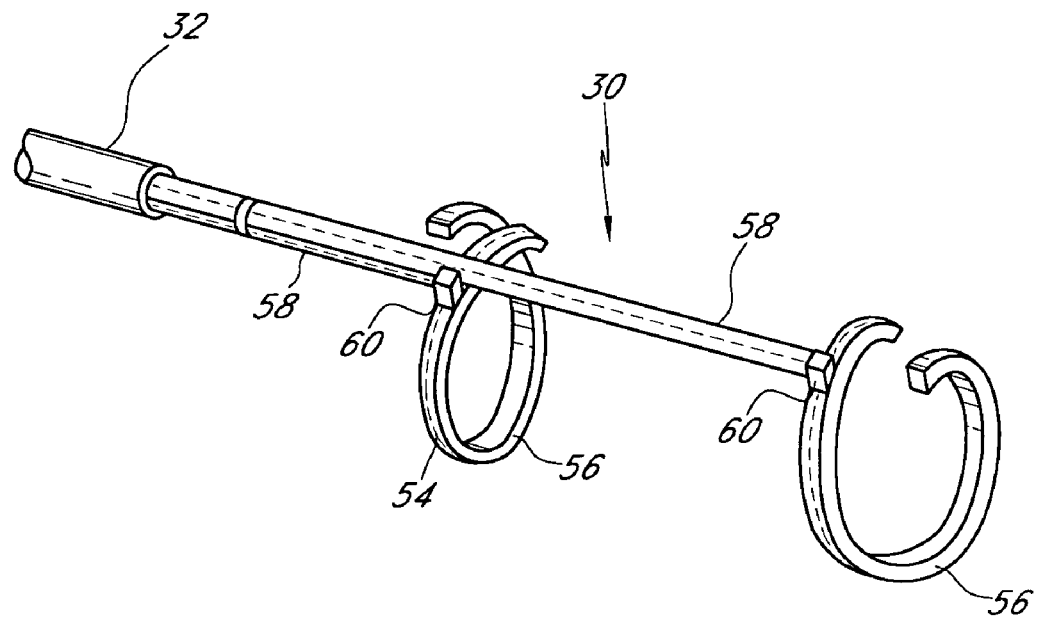
FIG. 5 is an enlarged perspective view of an embodiment of a cuff electrode configured to be coupled to a peripheral nerve of a patient.
Figure 6:
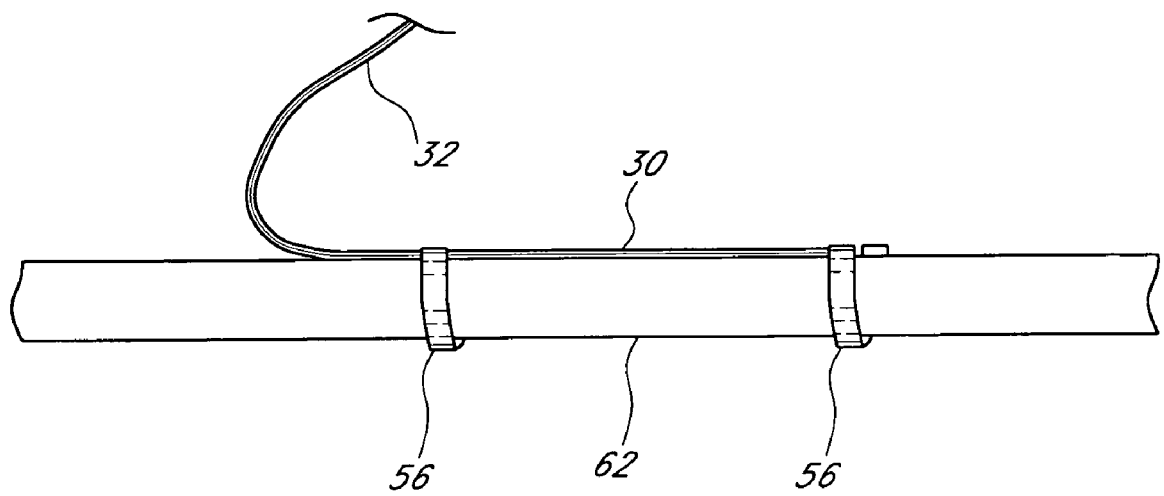
FIG. 6 is an elevational view of the cuff electrode of FIG. 5 coupled to a section of a peripheral nerve.

FIG. 5 illustrates an enlarged perspective view of the cuff electrode 30. The cuff electrode 30 is an example of an HMRI Bipolar Electrode manufactured by the HMRI Company in Pasadena, Calif. The cuff electrode 30 includes a silicone backing 54, a platinum-iridium ribbon 56, silicone covered leads 58 and welded junctions 60. The cuff electrode design allows the cuff rings 56 to be flexible and self-sizing, minimizes mechanical trauma to the nerve 62 and allows body fluid interchange with the nerve 62 as shown in FIG. 6. The electrode array consists of two separate coils 56 of platinum-iridium ribbon material that may have a platinum content of about 20% for some embodiments. Elongate and flexible electrical leads 58 are spot welded or otherwise secured in an electrically conducting relationship to each coil 56. The coils 56 are then placed into a mould, which is filled with a silicone elastomer gel that has been approved for long-term implantation that, after curing, becomes the silicone backing 54 of each coil 56.

The silicone, which is known as the carrier, provides the array with sufficient elasticity to be opened by the Application Forceps (not shown) and enough memory that it will return to a size that will fit snugly enough to provide efficient contact for electrostimulation of a nerve 62 without causing mechanical injury to the nerve 62. The silicone carrier also seals the area where the wire is welded to the ribbon, thereby reducing the potential for electrolysis or corrosion due to the junction of dissimilar metals. Finally, since the silicone covers all aspects of the ribbon other than the surface that is applied to the nerve 62, it fully insulates the surrounding tissues from any electrical impulses. The spiral helices are formed so that one coil 56 is slightly clockwise and the other coil 56 slightly counterclockwise. This reduces longitudinal movement along the nerve 62. Coils 56 can be made with different diameters, depending on the nerve to be implanted. The vagus and splanchnic nerves for some patients may have an outer transverse dimension or diameter of about 4.0 mm to about 5.25 mm. Although the cuff electrode embodiment 30 shown in FIG. 5 is a bipolar electrode, embodiments of tissue stimulation devices discussed herein may also include monopolar electrode embodiments. In addition, multiple electrodes, either bipolar or monopolar, or any combination thereof may be used to provide stimulation.

Figure 7:
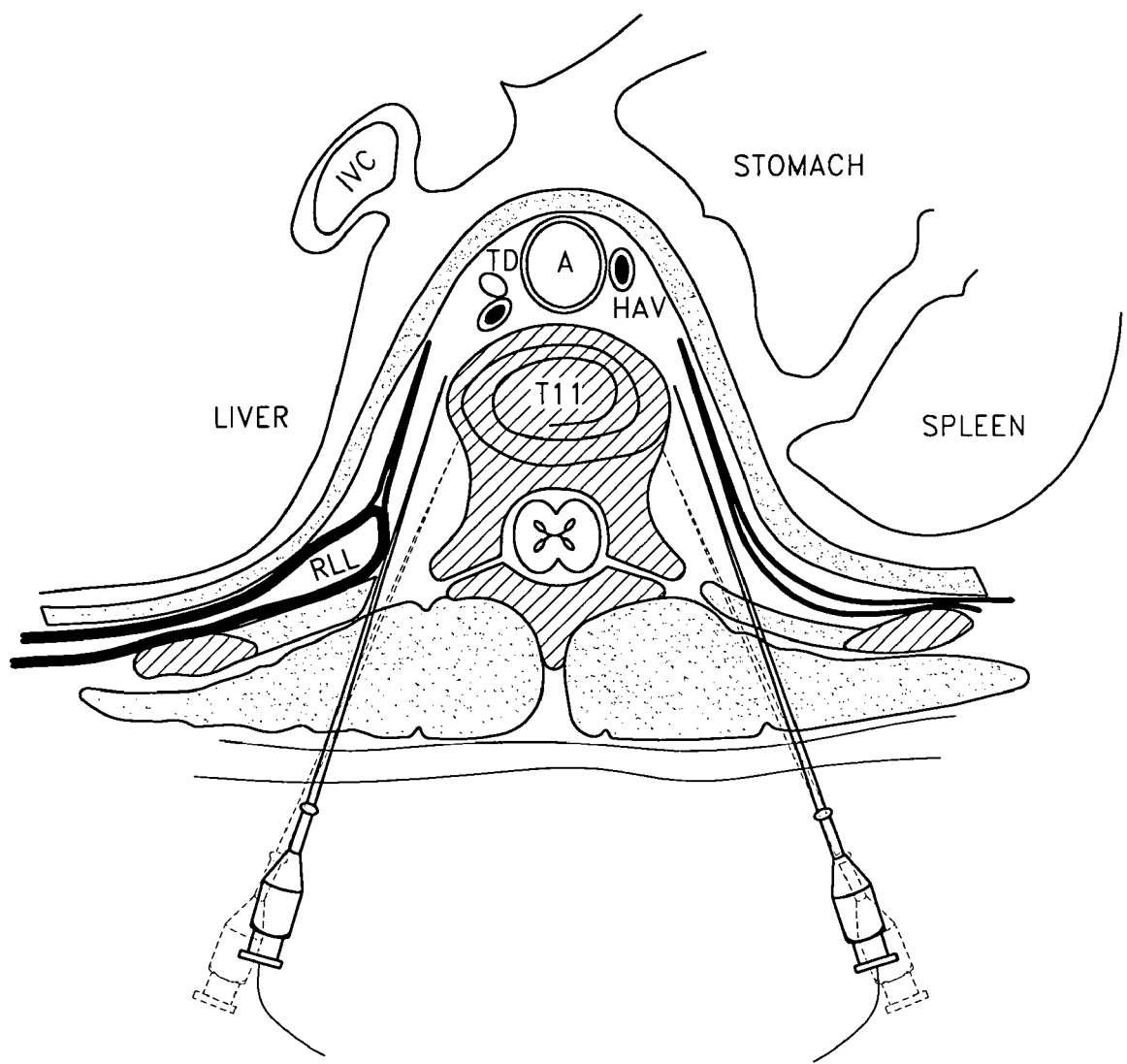
FIG. 7 is a cross sectional view of the spinal region of a patient illustrating the insertion of a thorascopic deployment device for deployment of a cuff electrode and electrical leads.

Both the electrode 30 and the IPG 28 may be placed surgically. While many options are available to clinicians, one method embodiment will involve an endoscopic procedure utilizing a thorascope to place the distal tip of the electrode 30 around a target nerve in the lower thoracic cavity or upper abdominal cavity from a posterior lateral approach as shown in FIG. 7. Once the electrode is placed, a tunneling tool will be used to create a channel through which the leads will be placed leading to the IPG 28. A sub-cutaneous pocket may be created in the so-called "love-handle" hip area of the patient for placement of the IPG 28. The IPG 28 may then be placed in this pocket. Thereafter, the lead 32 may be attached or otherwise electrically coupled to the IPG 28 and the pocket closed by standard operating procedures. This surgical procedure embodiment is only provided for example and should not limit the procedure to alternate surgical procedures.

Figure 8:
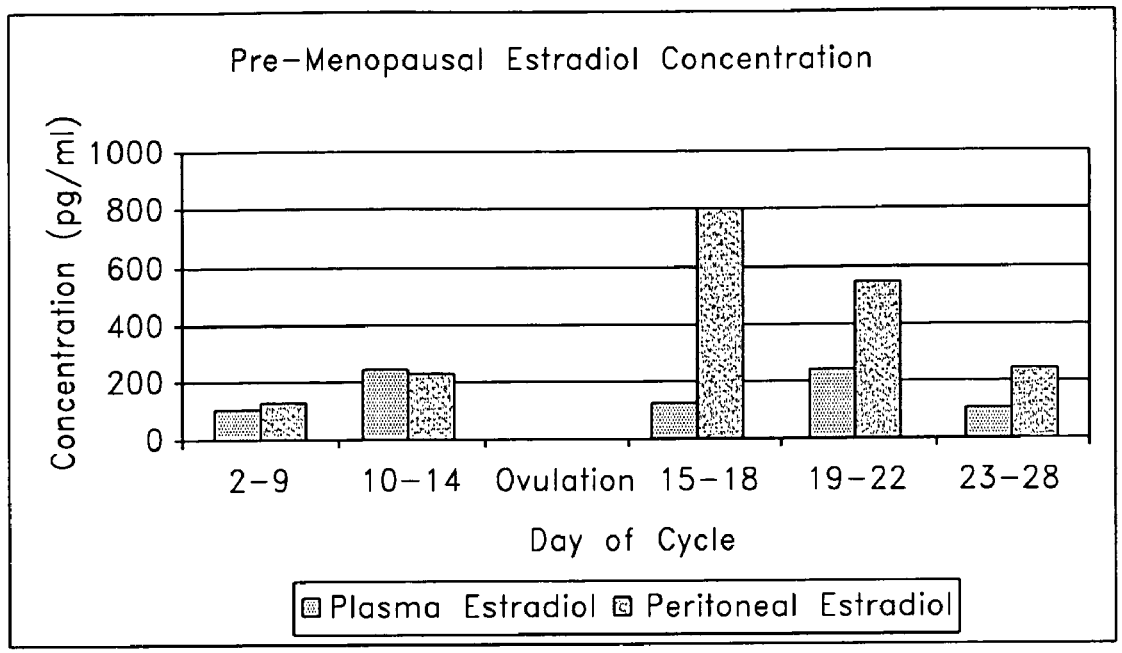
FIG. 8 shows a table of pre-menopausal estradiol concentrations with respect to the days of a menstrual cycle.
Figure 9:
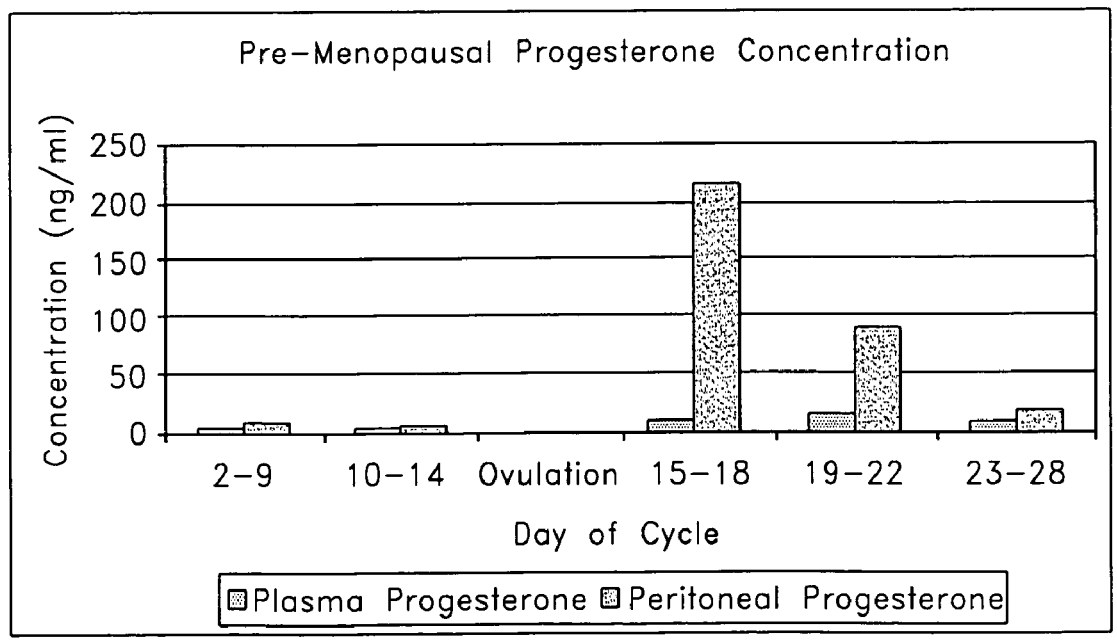
FIG. 9 shows a table of pre-menopausal progesterone concentrations with respect to the days of a menstrual cycle.

Once the surgical placement of the tissue stimulation device is completed and a recovery time is allowed, a programmed tissue stimulation pattern may begin being applied to a target nerve by activation of the IPG 28. The IPG may be activated or otherwise turned on directly or indirectly through the use of a telemetry wand that non-invasively communicates with the IPG 28. A static or dynamic tissue stimulation pattern may be chosen to produce desired or predetermined hormone level patterns in the patient. As discussed above, some hormone level pattern embodiments are configured to be useful for the treatment of menopause. The logic and control unit 42 controls the tissue stimulation output or dose and includes a memory unit that may store machine readable information which allows for programming of the various tissue stimulation patterns that determine the tissue stimulation energy parameters over time including the signal voltage, frequency, pulse width, duty cycle and the like. The tissue stimulation pattern and corresponding tissue stimulation energy parameters determine or modulate the hormone production levels over time to generate a desired hormone level pattern. FIGS. 8 and 9 show examples of two hormone level patterns of interest that may be produced for treatment of menopause or other gynecological conditions. It should not be construed that these are the only hormone level patterns to be induced or that these hormones cannot be replaced with other hormones of interest. They are only provided to be illustrative.

For some embodiments it may be desirable to provide hormone level measurement feedback to the device in the form of a control loop that allows for adjustment of stimulation levels in response to reference hormone levels of preselected hormones. Preferably, the hormone levels are measured by analyzing body fluids such as urine or serum. Such measurement may be performed by urinalysis or other means with the hormone level data entered or otherwise transferred to the processor of the IPG 28. If a desired hormone level is too low compared to a reference level, the tissue stimulation dose or electrical dose may be increased in order to accommodate an upward adjustment in production of that hormone. Likewise, if a desired hormone level is too high with respect to a reference level, the tissue stimulation dose or electrical dose may be decreased in order to decrease the hormone production. The hormone level data or pattern of the tables shown in FIGS. 8 and 9 may be used as hormone reference levels for feedback loop adjustment in some embodiments.

Based on known stimulation technologies for similarly sized and configured nerves, the stimulation energy parameters or dose for some embodiments of systems and methods for the regulation of gynecologic hormone regulation may include a frequency between about 1 and about 50 Hz, a pulse width between about 125 and about 1,000 μsec, a current amplitude up to about 5.0 mA (this current amplitude may be held constant (static) or varied (dynamic) over time between the low and high amplitude), and a duty cycle between about 5% and about 60%. In other embodiments, the frequency of a stimulation signal may be from about 5 Hz to about 30 Hz, specifically, about 10 Hz to about 20 Hz. In some embodiments, the pulse width of a stimulation energy signal may be from about 250 microseconds to about 750 microseconds, specifically, from about 400 microseconds to about 600 microseconds. In some embodiments, the current magnitude of a stimulation energy signal may be up to about 10 mA. In some embodiments, the duty cycle of a stimulation signal may be from about 10% to about 50%, specifically, from about 25% to about 50%.

Any of the above stimulation energy parameters may be varied or multiple stimulation energy parameters may be varied to prevent habituation of the endocrine system to the stimulation. The variation of the stimulation energy parameters may be varied in a cyclic fashion to vary the concentration of hormones of interest produced. Any of the above stimulation energy parameters may also be held constant throughout a tissue stimulation pattern. A dynamic tissue stimulation pattern or algorithm may produce a pattern of hormone production that prevents the side effects associated with PPM, while producing enough hormones to emulate the pre-menopause production cycle. It is anticipated that a dynamic electrical tissue stimulation pattern will be most effective in the treatment of menopause and other gynecological conditions, but static tissue stimulation patterns may be used as an effective embodiment.

Since the production of hormones is stimulation or electrical energy dose-dependent, higher stimulation energy doses will lead to greater production of hormones. The requirement of hormone levels varies over the entire estrus cycle; therefore, the electrical tissue stimulation pattern may also vary to match the hormone level or production pattern for a desired result. Although these tissue stimulation energy signals are indicated for application to an autonomic parasympathetic peripheral nerve of a patient, such as the vagus nerve or an autonomic sympathetic nerve such as the splanchnic nerve, the same or similar tissue stimulation energy signals or patterns may also be applied to other tissues to achieve the same or similar results. For example, such tissue stimulation patterns or energy signals may be applied to the ovarian nerve, to an organ such as an adrenal gland, including, specifically, the adrenal cortex or adrenal medulla, the ovaries, ovum, uterus, peri-abdominal fat, the hypothalamus and the pituitary gland as well as others. In addition, the nerves that innervate any of the above tissues or organs may also be stimulated with any of the tissue stimulation patterns or tissue stimulation energy parameters discussed herein.

For some treatment embodiments, concentrations of both estradiol and progesterone remain low for the first 14 days of the estrus cycle. This is the point where ovulation occurs.

Days 15 to 18 see a sharp rise in levels of both hormones. The concentrations of both hormones then decrease from Day 19 to Day 28. The post menopausal woman show a marked decrease in both estradiol and progesterone. To achieve these hormone levels, initially low levels of an electrical stimulation energy dose will be required followed by an increase in stimulation energy dose then followed by a decrease in electrical stimulation energy dose. Some potential tissue stimulation patterns are proposed below.

Two examples of tissue stimulation patterns or profile embodiments contemplated for the methods and devices discussed above are shown in FIGS. 10 and 11. Referring to a dynamic tissue stimulation pattern shown in FIG. 10, the current is changed or adjusted to reflect estradiol and progesterone demand. After Day 28 the pattern is then repeated. In some embodiments, a stimulation energy dose is initiated and increased from about day 1 to about day 14 of the tissue stimulation pattern, held substantially constant from about day 15 to about day 18 of the tissue stimulation pattern and decreased from about day 19 to about day 28 of the tissue stimulation pattern. The tissue stimulation pattern may then be repeated for an additional cycle or as many 28 day cycles as desired. In some other embodiments, a stimulation energy dose is initiated in a tissue stimulation pattern and increased from about day 1 to about day 7 of the tissue stimulation pattern, held substantially constant from about day 8 to about day 24 of the tissue stimulation pattern and decreased from about day 25 to about day 28 of the tissue stimulation pattern. This tissue stimulation pattern may then be repeated once or for as many 28 day cycles as desired. For yet some other embodiments, a stimulation energy dose or electrical dose is initiated according to a tissue stimulation pattern and increased from about day 1 to about day 7 of the tissue stimulation pattern, held substantially constant from about day 8 to about day 28 of the tissue stimulation pattern and thereafter held substantially constant for as long as desired or indefinitely.

A substantially static tissue stimulation pattern as indicated in the table shown in FIG. 11 provides a higher level of induced hormone production for a larger portion of the tissue stimulation pattern than the induced hormone production of the tissue stimulation pattern indicated by the table in FIG. 10. Referring to the stimulation pattern of FIG. 11, after Day 28 the stimulation pattern is repeated or high level stimulation with an electrical current of about 3.0 mA to about 4.0mA is continued indefinitely from Day 24 forward for ongoing static tissue stimulation pattern. It should noted that the frequency of some stimulation energy dose embodiments may also be varied from about 1 Hz to about 50 Hz, the pulse width may be varied from about 125 microseconds to about 1,000 microseconds and/or the duty cycle may be varied from about 5% to about 60%. An electrical stimulation energy dose is defined herein as the multiplicative combination of all relevant electrical stimulation parameters. For example the electrical dose for a stimulation signal having a frequency of 20 Hz, a pulse width of 500 μsec, a current amplitude of 3.0 mA, and a duty cycle of 50% is 0.015 mA-sec or 20 Hz×0.0005 seconds×3.0 mA×0.5). An increase in any single stimulation energy parameter or combination of stimulation energy parameters will result in an increase in the electrical stimulation dose.

One concern with regard to stimulation of either the vagus nerve or splanchnic nerve may be the effect of such stimulation on cardiac functions of the patient. Common side effects of such stimulation may include increased heart rate and increased blood pressure which may have deleterious effects over an extended period of time. In order to minimize cardiac side effects or complications, it may be desirable to locate the electrode as low as possible along the vagus nerve and as close to the target organ, such as the adrenal cortex, in order to minimize efferent neural signals reverting back to the central nervous system (CNS) which may then travel to the heart and surrounding tissue. Another method of minimizing cardiac side effects is to select a stimulation duty cycle that is less than about 50%. For example, duty cycles of stimulation energy may be from about 10 percent to about 50 percent. Some embodiments include a method of electrically stimulating tissues to induce hormone production to treat gynecological conditions without causing any significant increase in mean arterial pressure and heart rate.

For some embodiments, it may be desirable to configure tissue stimulation patterns or other treatment parameters, electrode placement or both to keep any increase in mean arterial pressure due to the treatment to less than about 25% of the nominal mean arterial pressure without treatment. For some embodiments, it may be desirable to configure tissue stimulation patterns, electrode placement or both to keep any increase in heart rate due to the treatment to less than about 25% of the nominal heart rate without treatment. Some embodiments include a method of electrical stimulation, as described above, causing desired hormone up- and down-regulation without causing significant changes in important vital signs such as blood pressure, heart rate, and body temperature. For some embodiments, the change in important vital signs may be up to about 30%, specifically, up to about 25%.

With regard to birth control, the effectiveness of current birth control modalities is limited by consistent use or patient compliance. Use of a tissue stimulation device such as an electrical tissue stimulation device may apply tissue stimulation patterns to promote the up- and down-regulation of hormones related to the estrus cycle in quantities comparable to those delivered by present birth control to eliminate the compliance issue while providing effective birth control. The same tissue stimulation device embodiments described above for management of PPM can be used for this indication. Embodiments relate to a method of treating a gynecological condition such as altering the normal estrus cycle through the endogenous production of hormones, such as estrogen, progesterone and their precursors, through electrical stimulation to prevent pregnancy in mammals. The well documented hormone level pattern requirements, as induced by the administration of standard birth control pills, may be achieved through the application of dynamic or static tissue stimulation patterns. Hormone level patterns can be induced through dynamic or static tissue stimulation patterns to produce enough hormone quantities to prevent fertilization and pregnancy, while limiting the production of hormones to prevent side effects. Some tissue stimulation pattern embodiments include a method of electrical stimulation to manage the estrus cycle in a way to prevent conception (birth control) through electrical stimulation of tissue to induce production of endogenous hormones such as estrogen, progesterone, estradiol, pregnenolone, androstenedione, androgens, and progestins and their precursors.

A life-long or long term therapy can be envision where the implant of a tissue stimulation device is made early in the life of a woman and functions as a birth control device until the time in her life when menopause management is required or she desires to conceive. A tissue stimulation pattern, which may be stored in the memory unit of a tissue stimulation device in the form of a software program, can be replaced or modified through non-invasive telemetry from the birth control tissue stimulation algorithm or pattern to a PPM tissue stimulation algorithm or pattern required to manage of menopause (PPM). If at any time the woman wished to become pregnant after the implantation of the device but prior to menopause, the device can be turned off via non-invasive telemetry, so the normal pattern of endogenous hormone production can return and the woman is able to conceive. After giving birth, the tissue stimulation pattern for birth control can be non-invasively reactivated to resume the birth control function. Embodiments relate to a series of methods of treating the evolving medical gynecological conditions of interrupting estrus, re-establishing normal estrus, interrupting estrus for at least a second time and changing the treatment algorithm to reduce or prevent the side-effects associated with menopause as the menopausal phase of life begins.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method of treating gynecological conditions in a body of a mammal, comprising:
   stimulating tissue at a first stimulation energy dose to induce a production of at least one gynecologic hormone, the first stimulation energy dose having at least one frequency, at least one pulse width, at least one duty cycle and at least one intensity;
   measuring a concentration of the at least one gynecologic hormone in the body of the mammal;
   comparing the measured concentration of the at least one gynecologic hormone against a desired reference concentration;
   adjusting the first stimulation energy dose according to any measured difference in concentration between the desired reference concentration and the measured concentration; and
   stimulating tissue at an adjusted stimulation energy dose having at least one frequency, at least one pulse width, at least one duty cycle and at least one intensity,
   wherein the stimulating is performed by a tissue stimulation device comprising a memory unit with machine readable information representing a desired hormone level pattern and wherein comparing the measured concentration against the desired reference concentration comprises comparing the measured concentration against the desired hormone level pattern; and
   wherein the desired hormone level pattern comprises a pre-menopausal hormone level pattern for a human female.

2. The method of claim 1, further comprising:
   surgically implanting the tissue stimulation device.

3. The method of claim 1 wherein the desired hormone level pattern comprises a pattern of hormone levels corresponding to a typical estrus cycle pattern of hormone levels.

4. The method of claim 3 wherein the desired hormone level pattern is about 26 to about 30 days in duration.

5. The method of claim 1 wherein the at least one gynecologic hormone is selected from the group consisting of estrogen, progesterone, estradiol, pregnenolone, androstenedione, estrone, androgens, and progestins.

6. The method of claim 1 wherein the at least one frequency of the adjusted stimulation energy dose is from about 1 Hz to about 50 Hz.

7. The method of claim 1 wherein stimulation occurs without raising the baseline mean arterial pressure of the mammal by more than 25%.

8. The method according to claim 1, wherein the pulse width of the first energy stimulation dose comprises from about 125 microseconds to about 1000 microseconds.

9. The method according to claim 1, wherein the intensity of the first energy stimulation dose comprises up to about 10 mAmps.

10. The method according to claim 1, wherein the duty cycle of the first energy stimulation dose comprises from about 5 to about 60%.

11. The method according to claim 1, wherein the pulse width of the adjusted energy stimulation dose comprises from about 125 microseconds to about 1000 microseconds.

12. The method according to claim 1, wherein the intensity of the adjusted energy stimulation dose comprises up to about 10 mAmps.

13. The method according to claim 1, wherein the duty cycle of the adjusted energy stimulation dose comprises from about 5 to about 60%.

14. The method according to claim 1, wherein the stimulated tissue comprises a vagus nerve, an autonomic sympathetic nerve, a splanchnic nerve, an ovarian nerve, an adrenal gland, an adrenal cortex, an adrenal medulla, an ovary, a uterus, a pen-abdominal fat, a hypothalamus or a pituitary.

15. A method of treating multiple gynecology conditions in a mammal, comprising, electrically stimulating tissues with multiple tissue stimulation patterns having at least one frequency, at least one pulse width, at least one intensity and at least one duty cycle, so as to alter hormone production of the mammal, wherein the gynecological conditions comprise interruption of the estrus cycle to prevent pregnancy, resumption of normal estrus through interruption of electrical tissue stimulation to allow a resumption of a normal estrus cycle and conception.

16. The method of claim 15 wherein stimulation occurs without raising the baseline heart rate of the mammal by more than 25%.

17. The method of claim 15, further comprising surgically implanting a programmable electrical tissue stimulation energy source that provides electrical stimulation with stimulation parameters that are controllable and repeatable.

18. The method of claim 15, wherein the electrical stimulation for the treatment of menopause follows a tissue stimulation pattern configured to induce production of a pattern of hormone levels corresponding to a typical estrus cycle pattern of hormone levels.

19. The method of claim 18, wherein the typical estrus cycle and pattern of hormone levels is about 26 to about 30 days in duration.

20. The method of claim 15, wherein the multiple tissue stimulation patterns alter the hormone production of at least one hormone selected from the group consisting of estrogen, progesterone, estradiol, pregnenolone, androstenedione, estrone, androgens, and progestins.

21. The method of claim 15, wherein the at least one frequency of the multiple tissue stimulation patterns is from about 1 Hz to about 50 Hz.

22. The method according to claim 15, wherein the at least one pulse width of the multiple stimulation patterns comprises from about 125 microseconds to about 1000 microseconds.

23. The method according to claim 15, wherein the at least one intensity of the multiple stimulation patterns comprises up to about 10 mAmps.

24. The method according to claim 15, wherein the at least one duty cycle comprises from about 5 to about 60%.

25. The method according to claim 15, wherein the stimulated tissues comprise a vagus nerve, an autonomic sympathetic nerve, a splanchnic nerve, an ovarian nerve, an adrenal gland, an adrenal cortex, an adrenal medulla, an ovary, a uterus, a pen-abdominal fat, a hypothalamus or a pituitary.

26. A method of treating multiple gynecology conditions in a mammal, comprising, electrically stimulating tissues with multiple tissue stimulation patterns having at least one frequency, at least one pulse width, at least one intensity and at least one duty cycle, so as to alter hormone production of the mammal, wherein the gynecological conditions comprise interruption of the estrus cycle and treatment of menopause and wherein the gynecological conditions are treated separately and sequentially.

27. The method of claim 26 wherein the tissue stimulation pattern for the treatment of menopause comprises: (a) increasing the electrical dose from about day 1 to about day 14; (b) holding the electrical dose substantially constant from about day 15 to about day 18; and (c) decreasing the electrical dose from about day 19 to about day 28.

28. The method of claim 27 further comprising repeating (a) through (c) at least once.

29. The method of claim 26 wherein the tissue stimulation pattern for the treatment of menopause comprises: (a) increasing the electrical dose from about day 1 to about day 7; (b) holding the electrical dose substantially constant from about day 8 to about day 24; and (c) decreasing the electrical dose from about day 25 to about day 28.

30. The method of claim 29 further comprising repeating (a) through (c) at least once.

31. The method of claim 26 wherein the tissue stimulation pattern for the treatment of menopause comprises: (a) increasing the electrical dose from about day 1 to about day 7; (b) holding the electrical dose substantially constant from about day 8 to about day 28; and (c) continuing to hold the electrical dose substantially constant beyond day 28.

32. The method of claim 31 further comprising continuing to hold the electrical dose substantially constant until treatment is terminated.

33. The method of claim 26, further comprising surgically implanting a programmable electrical tissue stimulation energy source that provides electrical stimulation with stimulation parameters that are controllable and repeatable.

34. The method of claim 26, wherein the multiple tissue stimulation patterns alter the production of at least one hormone selected from the group consisting of estrogen, progesterone, estradiol, pregnenolone, androstenedione, estrone, androgens, and progestins.

35. The method of claim 26, wherein the at least one frequency of the multiple tissue stimulation patterns is from about 1 Hz to about 50 Hz.

36. The method of claim 26, wherein stimulation occurs without raising the baseline mean arterial pressure of the mammal by more than 25%.

37. The method according to claim 26, wherein the at least one pulse width of the multiple stimulation patterns comprises from about 125 microseconds to about 1000 microseconds.

38. The method according to claim 26, wherein the at least one intensity of the multiple stimulation patterns comprises up to about 10 mAmps.

39. The method according to claim 26, wherein the at least one duty cycle comprises from about 5 to about 60%.

40. The method according to claim 26, wherein the stimulated tissues comprise a vagus nerve, an autonomic sympathetic nerve, a splanchnic nerve, an ovarian nerve, an adrenal gland, an adrenal cortex, an adrenal medulla, an ovary, a uterus, a pen-abdominal fat, a hypothalamus or a pituitary.

\* \* \* \* \*

UNITED STATES PATENT AND TRADEMARK OFFICE
CERTIFICATE OF CORRECTION

PATENT NO. : 7,623,924 B2
APPLICATION NO. : 11/215892
DATED : November 24, 2009
INVENTOR(S) : Hugh Louis Narciso, Jr.

It is certified that error appears in the above-identified patent and that said Letters Patent is hereby corrected as shown below:

Title Page; item (56);
On page 2, under "Other Publications", in column 2, line 8, delete "Ndrocrinology" and insert -- Endocrinology --, therefor.

On page 2, under "Other Publications", in column 2, line 13, delete "Reugulation" and insert -- Regulation --, therefor.

On page 2, under "Other Publications", in column 2, line 45, delete "Oesophagel" and insert -- Oesophageal --, therefor.

On page 2, under "Other Publications", in column 2, line 47, delete "Intakd" and insert -- Intake --, therefor.

On page 2, under "Other Publications", in column 2, line 53, delete "Spanchnic" and insert -- Splanchnic --, therefor.

On page 3, under "Other Publications", in column 1, line 22, delete "Neyral" and insert -- Neural --, therefor.

On page 3, under "Other Publications", in column 1, line 25, delete "Subcuraneous" and insert -- Subcutaneous --, therefor.

On page 3, under "Other Publications", in column 1, line 42, delete "Stimulatin" and insert -- Stimulation --, therefor.

On page 3, under "Other Publications", in column 2, line 23, delete "Neuorscience" and insert -- Neuroscience --, therefor.

On page 3, under "Other Publications", in column 2, line 26, delete "HCO3" and insert -- $HCO_3$ --, therefor.

On page 3, under "Other Publications", in column 2, line 38, delete "Electrophhysiology" and insert -- Electrophysiology --, therefor.

On page 3, under "Other Publications", in column 2, line 39, delete "Neurophsiol" and insert -- Neurophysiol --, therefor.

On page 3, under "Other Publications", in column 2, line 44, delete "Insuling, Somatosatin" and insert -- Insulin, Somatostatin --, therefor.

CERTIFICATE OF CORRECTION (continued)
U.S. Pat. No. 7,623,924 B2

On page 3, under "Other Publications", in column 2, line 68, delete "Metabolis" and insert -- Metabolic --, therefor.

On page 4, under "Other Publications", in column 1, line 15, delete "Summatino" and insert -- Summation --, therefor.

On page 4, under "Other Publications", in column 1, line 27, delete "Releast" and insert -- Release --, therefor.

On page 4, under "Other Publications", in column 1, line 37, delete "Intraveneous" and insert -- Intravenous --, therefor.

On page 4, under "Other Publications", in column 1, line 41, delete "Sato, T, et al.," and insert -- Sato, T. et al., --, therefor.

On page 4, under "Other Publications", in column 1, line 41, delete "Therepeutic" and insert -- Therapeutic --, therefor.

On page 4, under "Other Publications", in column 2, line 14, delete "Realease" and insert -- Release --, therefor.

On page 4, under "Other Publications", in column 2, line 39, delete "Physiolotical" and insert -- Physiological --, therefor.

In column 6, line 12, delete "me" and insert -- the --, therefor.

In column 6, line 47, delete "thorascopic" and insert -- thoracoscopic --, therefor.

In column 7, line 50-51, delete "thoracascopic" and insert -- thoracoscopic --, therefor.

In column 11, line 16, delete "thorascope" and insert -- thoracoscope --, therefor.

In column 16, line 26, in Claim 14, delete "pen" and insert -- peri --, therefor.

In column 17, line 7, in Claim 25, delete "pen" and insert -- peri --, therefor.

In column 18, line 34, in Claim 40, delete "pen" and insert -- peri --, therefor.

Signed and Sealed this

Sixteenth Day of March, 2010

David J. Kappos
*Director of the United States Patent and Trademark Office*